(12) United States Patent
Curran et al.

(10) Patent No.: US 6,323,177 B1
(45) Date of Patent: Nov. 27, 2001

(54) INTERACTION OF REELIN WITH VERY LOW DENSITY LIPOPROTEIN (VLDL) RECEPTOR FOR SCREENING AND THERAPIES

(75) Inventors: Thomas Curran; Gabriella D'Arcangelo, both of Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 09/334,220

(22) Filed: Jun. 16, 1999

(51) Int. Cl.[7] .......................... C07K 14/00; G01N 33/53; G01N 33/566

(52) U.S. Cl. ................... 514/8; 435/7.1; 435/7.2; 435/348; 435/325; 530/350

(58) Field of Search .................. 530/350; 435/7.1, 435/7.2, 325, 348; 514/8

(56) References Cited

PUBLICATIONS

Del Rio et al., Nature, 385:70–74, 1997.
Borrell et al., J. Neurosci., 19:1345–1358, 1999.
Howell et al., Genes and Dev., 13:643–648, 1999.
Trommsdorff et al., J. Biol. Chem., 273:33556–33560, 1999.
D'Arcangelo and Curran, Reeler: New Tales on an Old Mutant Mouse, BioEssays, In press, 1998.
Rice et al., Development 125:3719–3729, 1998.
Price and Sisodia, Ann. Rev. Neurosci., 21:479–505, 1998.
Royaux et al., Genomic Organization of the Mouse Reelin Gene, Genomics, In press, 1997.
DeSilva et al., Genome Res., 7:157–164, 1997.
Howell et al., EMBO J., 16:121–132, 1997.
Howell et al., Nature, 389:733–736, 1997.
Sheldon et al., Nature, 389:730–733, 1997.
Oshima et al., 1996; Chae et al., Neuron, 18:29–42, 1997.
Kim et al., J. Biol. Chem., 271:8373–8380, 1996.
Novak et al., J. Biol. Chem., 271:11732–11736, 1996.
Strittmatter and Roses, Proc. Natl. Acad. Sci. USA, 92:4725–4727, 1995.
Miao et al., Proc. Natl. Acad. Sci. USA, 91:11050–11054, 1994.
Takahashi et al., Proc. Natl. Acad. Sci. USA, 89:9252–9256, 1992.
Chae, et al., Neuron, 18:29–42, 1997.
Bergeyck, et al., "A panel of monoclonal antibodies against reelin, the extracellular matrix protein defective in reeler mutant mice", *Journal of Neuroscience Methods*, 1998, 82(1):17–24.
D'Arcangelo, et al., "Reelin Is a Secreted Glycoprotein Recognized by the CR–50 Monoclonal Antibody", *The Journal of Neuroscience*, 1997, 17(1):23–31.

Primary Examiner—Prema Mertz
Assistant Examiner—Joseph F. Murphy
(74) Attorney, Agent, or Firm—Darby & Darby

(57) ABSTRACT

Interaction between Reelin and the very low density lipoprotein (VLDL) receptor has been discovered. This allows development of a convenient assay system for receptor binding that is adaptable for screening modulators (agonists and antagonists) of the interaction between Reelin and the VLDL receptor or similar receptors.

17 Claims, 1 Drawing Sheet

SEQUENCE LISTING

<160> NUMBER OF SEQ ID NOS: 5

<210> SEQ ID NO 1
<211> LENGTH: 3460
<212> TYPE: PRT
<213> ORGANISM: Homo sapien

<400> SEQUENCE: 1

```
Met Glu Arg Ser Gly Trp Ala Arg Gln Thr Phe Leu Leu Ala Leu Leu
  1               5                  10                  15

Leu Gly Ala Thr Leu Arg Ala Arg Ala Ala Gly Tyr Tyr Pro Arg
                 20                  25                  30

Phe Ser Pro Phe Phe Phe Leu Cys Thr His His Gly Glu Leu Glu Gly
             35                  40                  45

Asp Gly Glu Gln Gly Glu Val Leu Ile Ser Leu His Ile Ala Gly Asn
 50                  55                  60

Pro Thr Tyr Tyr Val Pro Gly Gln Glu Tyr His Val Thr Ile Ser Thr
 65                  70                  75                  80

Ser Thr Phe Phe Asp Gly Leu Leu Val Thr Gly Leu Tyr Thr Ser Thr
                 85                  90                  95

Ser Val Gln Ala Ser Gln Ser Ile Gly Gly Ser Ser Ala Phe Gly Phe
                100                 105                 110

Gly Ile Met Ser Asp His Gln Phe Gly Asn Gln Phe Met Cys Ser Val
                115                 120                 125

Val Ala Ser His Val Ser His Leu Pro Thr Thr Asn Leu Ser Phe Ile
    130                 135                 140

Trp Ile Ala Pro Pro Ala Gly Thr Gly Cys Val Asn Phe Met Ala Thr
145                 150                 155                 160

Ala Thr His Arg Gly Gln Val Ile Phe Lys Asp Ala Leu Ala Gln Gln
                165                 170                 175

Leu Cys Glu Gln Gly Ala Pro Thr Asp Val Thr Val His Pro His Leu
                180                 185                 190

Ala Glu Ile His Ser Asp Ser Ile Ile Leu Arg Asp Asp Phe Asp Ser
            195                 200                 205

Tyr His Gln Leu Gln Leu Asn Pro Asn Ile Trp Val Glu Cys Asn Asn
        210                 215                 220

Cys Glu Thr Gly Glu Gln Cys Gly Ala Ile Met His Gly Asn Ala Val
225                 230                 235                 240

Thr Phe Cys Glu Pro Tyr Gly Pro Arg Glu Leu Ile Thr Thr Gly Leu
                245                 250                 255

Asn Thr Thr Thr Ala Ser Val Leu Gln Phe Ser Ile Gly Ser Gly Ser
                260                 265                 270

Cys Arg Phe Ser Tyr Ser Asp Pro Ser Ile Ile Val Leu Tyr Ala Lys
            275                 280                 285

Asn Asn Ser Ala Asp Trp Ile Gln Leu Glu Lys Ile Arg Ala Pro Ser
        290                 295                 300

Asn Val Ser Thr Ile Ile His Ile Leu Tyr Leu Pro Glu Asp Ala Lys
305                 310                 315                 320

Gly Glu Asn Val Gln Phe Gln Trp Lys Gln Glu Asn Leu Arg Val Gly
                325                 330                 335

Glu Val Tyr Glu Ala Cys Trp Ala Leu Asp Asn Ile Leu Ile Ile Asn
                340                 345                 350
```

-continued

```
Ser Ala His Arg Gln Val Val Leu Glu Asp Ser Leu Asp Pro Val Asp
            355                 360                 365

Thr Gly Asn Trp Leu Phe Phe Pro Gly Ala Thr Val Lys His Ser Cys
370                 375                 380

Gln Ser Asp Gly Asn Ser Ile Tyr Phe His Gly Asn Glu Gly Ser Glu
385                 390                 395                 400

Phe Asn Phe Ala Thr Thr Arg Asp Val Asp Leu Ser Thr Glu Asp Ile
                405                 410                 415

Gln Glu Gln Trp Ser Glu Glu Phe Glu Ser Gln Pro Thr Gly Trp Asp
            420                 425                 430

Val Leu Gly Ala Val Ile Gly Thr Glu Cys Gly Thr Ile Glu Ser Gly
            435                 440                 445

Leu Ser Met Val Phe Leu Lys Asp Gly Glu Arg Lys Leu Cys Thr Pro
450                 455                 460

Ser Met Asp Thr Thr Gly Tyr Gly Asn Leu Arg Phe Tyr Phe Val Met
465                 470                 475                 480

Gly Gly Ile Cys Asp Pro Gly Asn Ser His Glu Asn Asp Ile Ile Leu
                485                 490                 495

Tyr Ala Lys Ile Glu Gly Arg Lys Glu His Ile Thr Leu Asp Thr Leu
            500                 505                 510

Ser Tyr Ser Ser Tyr Lys Val Pro Ser Leu Val Ser Val Val Ile Asn
            515                 520                 525

Pro Glu Leu Gln Thr Pro Ala Thr Lys Phe Cys Leu Arg Gln Lys Asn
530                 535                 540

His Gln Gly His Asn Arg Asn Val Trp Ala Val Asp Phe His Val
545                 550                 555                 560

Leu Pro Val Leu Pro Ser Thr Met Ser His Met Ile Gln Phe Ser Ile
                565                 570                 575

Asn Leu Gly Cys Gly Thr His Gln Pro Gly Asn Ser Val Ser Leu Glu
            580                 585                 590

Phe Ser Thr Asn His Gly Arg Ser Trp Ser Leu Leu His Thr Glu Cys
            595                 600                 605

Leu Pro Glu Ile Cys Ala Gly Pro His Leu Pro His Ser Thr Val Tyr
610                 615                 620

Ser Ser Glu Asn Tyr Ser Gly Trp Asn Arg Ile Thr Ile Pro Leu Pro
625                 630                 635                 640

Asn Ala Ala Leu Thr Arg Asn Thr Arg Ile Arg Trp Arg Gln Thr Gly
                645                 650                 655

Pro Ile Leu Gly Asn Met Trp Ala Ile Asp Asn Val Tyr Ile Gly Pro
            660                 665                 670

Ser Cys Leu Lys Phe Cys Ser Gly Arg Gly Gln Cys Thr Arg His Gly
            675                 680                 685

Cys Lys Cys Asp Pro Gly Phe Ser Gly Pro Ala Cys Glu Met Ala Ser
690                 695                 700

Gln Thr Phe Pro Met Phe Ile Ser Glu Ser Phe Gly Ser Ser Arg Leu
705                 710                 715                 720

Ser Ser Tyr His Asn Phe Tyr Ser Ile Arg Gly Ala Glu Val Ser Phe
                725                 730                 735

Gly Cys Gly Val Leu Ala Ser Gly Lys Ala Leu Val Phe Asn Lys Glu
            740                 745                 750

Gly Arg Arg Gln Leu Ile Thr Ser Phe Leu Asp Ser Ser Gln Ser Arg
            755                 760                 765
```

-continued

```
Phe Leu Gln Phe Thr Leu Arg Leu Gly Ser Lys Ser Val Leu Ser Thr
    770                 775                 780

Cys Arg Ala Pro Asp Gln Pro Gly Glu Gly Val Leu Leu His Tyr Ser
785                 790                 795                 800

Tyr Asp Asn Gly Ile Thr Trp Lys Leu Leu Glu His Tyr Ser Tyr Leu
                805                 810                 815

Ser Tyr His Glu Pro Arg Ile Ile Ser Val Glu Leu Pro Gly Asp Ala
            820                 825                 830

Lys Gln Phe Gly Ile Gln Phe Arg Trp Trp Gln Pro Tyr His Ser Ser
        835                 840                 845

Gln Arg Glu Asp Val Trp Ala Ile Asp Glu Ile Ile Met Thr Ser Val
    850                 855                 860

Leu Phe Asn Ser Ile Ser Leu Asp Phe Thr Asn Leu Val Glu Val Thr
865                 870                 875                 880

Gln Ser Leu Gly Phe Tyr Leu Gly Asn Val Gln Pro Tyr Cys Gly His
                885                 890                 895

Asp Trp Thr Leu Cys Phe Thr Gly Asp Ser Lys Leu Ala Ser Ser Met
            900                 905                 910

Arg Tyr Val Glu Thr Gln Ser Met Gln Ile Gly Ala Ser Tyr Met Ile
        915                 920                 925

Gln Phe Ser Leu Val Met Gly Cys Gly Gln Lys Tyr Thr Pro His Met
    930                 935                 940

Asp Asn Gln Val Lys Leu Glu Tyr Ser Thr Asn His Gly Leu Thr Trp
945                 950                 955                 960

His Leu Val Gln Glu Glu Cys Leu Pro Ser Met Pro Ser Cys Gln Glu
                965                 970                 975

Phe Thr Ser Ala Ser Ile Tyr His Ala Ser Glu Phe Thr Gln Trp Arg
            980                 985                 990

Arg Val Ile Val Leu Leu Pro Gln Lys Thr Trp Ser Ser Ala Thr Arg
        995                 1000                1005

Phe Arg Trp Ser Gln Ser Tyr Tyr Thr Ala Gln Asp Glu Trp Ala Leu
    1010                1015                1020

Asp Ser Ile Tyr Ile Gly Gln Gln Cys Pro Asn Met Cys Ser Gly His
1025                1030                1035                1040

Gly Ser Cys Asp His Gly Ile Cys Arg Cys Asp Gln Gly Tyr Gln Gly
                1045                1050                1055

Thr Glu Cys His Pro Glu Ala Ala Leu Pro Ser Thr Ile Met Ser Asp
            1060                1065                1070

Phe Glu Asn Gln Asn Gly Trp Glu Ser Asp Trp Gln Glu Val Ile Gly
        1075                1080                1085

Gly Glu Ile Val Lys Pro Glu Gln Gly Cys Gly Val Ile Ser Ser Gly
    1090                1095                1100

Ser Ser Leu Tyr Phe Ser Lys Ala Gly Lys Arg Gln Leu Val Ser Trp
1105                1110                1115                1120

Asp Leu Asp Thr Ser Trp Val Asp Phe Val Gln Phe Tyr Ile Gln Ile
                1125                1130                1135

Gly Gly Glu Ser Ala Ser Cys Asn Lys Pro Asp Ser Arg Glu Glu Gly
            1140                1145                1150

Val Leu Leu Gln Tyr Ser Asn Asn Gly Gly Ile Gln Trp His Leu Leu
        1155                1160                1165

Ala Glu Met Tyr Phe Ser Asp Phe Ser Lys Pro Arg Phe Val Tyr Leu
    1170                1175                1180
```

-continued

```
Glu Leu Pro Ala Ala Ala Lys Thr Pro Cys Thr Arg Phe Arg Trp Trp
1185                1190                1195                1200

Gln Pro Val Phe Ser Gly Glu Asp Tyr Asp Gln Trp Ala Val Asp Asp
                1205                1210                1215

Ile Ile Ile Leu Ser Glu Lys Gln Lys Gln Ile Ile Pro Val Ile Asn
                1220                1225                1230

Pro Thr Leu Pro Gln Asn Phe Tyr Glu Lys Pro Ala Phe Asp Tyr Pro
            1235                1240                1245

Met Asn Gln Met Ser Val Trp Leu Met Leu Ala Asn Glu Gly Met Val
        1250                1255                1260

Lys Asn Glu Thr Phe Cys Ala Ala Thr Pro Ser Ala Met Ile Phe Gly
1265                1270                1275                1280

Lys Ser Asp Gly Asp Arg Phe Ala Val Thr Arg Asp Leu Thr Leu Lys
                1285                1290                1295

Pro Gly Tyr Val Leu Gln Phe Lys Leu Asn Ile Gly Cys Ala Asn Gln
                1300                1305                1310

Phe Ser Ser Thr Ala Pro Val Leu Leu Gln Tyr Ser His Asp Ala Gly
            1315                1320                1325

Met Ser Trp Phe Leu Val Lys Glu Gly Cys Tyr Pro Ala Ser Ala Gly
        1330                1335                1340

Lys Gly Cys Glu Gly Asn Ser Arg Glu Leu Ser Glu Pro Thr Met Tyr
1345                1350                1355                1360

His Thr Gly Asp Phe Glu Glu Trp Thr Arg Ile Thr Val Ile Pro
                1365                1370                1375

Arg Ser Leu Ala Ser Ser Lys Thr Arg Phe Arg Trp Ile Gln Glu Ser
            1380                1385                1390

Ser Ser Gln Lys Asn Val Pro Pro Phe Gly Leu Asp Gly Val Tyr Ile
        1395                1400                1405

Ser Glu Pro Cys Pro Ser Tyr Cys Ser Gly His Gly Asp Cys Ile Ser
        1410                1415                1420

Gly Val Cys Phe Cys Asp Leu Gly Tyr Thr Ala Ala Gln Gly Thr Cys
1425                1430                1435                1440

Val Ser Asn Val Pro Asn His Asn Glu Met Phe Asp Arg Phe Glu Gly
                1445                1450                1455

Lys Leu Ser Pro Leu Trp Tyr Lys Ile Thr Gly Ala Gln Val Gly Thr
            1460                1465                1470

Gly Cys Gly Thr Leu Asn Asp Gly Lys Ser Leu Tyr Phe Asn Gly Pro
            1475                1480                1485

Gly Lys Arg Glu Ala Arg Thr Val Pro Leu Asp Thr Arg Asn Ile Arg
        1490                1495                1500

Leu Val Gln Phe Tyr Ile Gln Ile Gly Ser Lys Thr Ser Gly Ile Thr
1505                1510                1515                1520

Cys Ile Lys Pro Arg Thr Arg Asn Glu Gly Leu Ile Val Gln Tyr Ser
                1525                1530                1535

Asn Asp Asn Gly Ile Leu Trp His Leu Leu Arg Glu Leu Asp Phe Met
                1540                1545                1550

Ser Phe Leu Glu Pro Gln Ile Ile Ser Ile Asp Leu Pro Gln Asp Ala
            1555                1560                1565

Lys Thr Pro Ala Thr Ala Phe Arg Trp Trp Gln Pro Gln His Gly Lys
        1570                1575                1580

His Ser Ala Gln Trp Ala Leu Asp Asp Val Leu Ile Gly Met Asn Asp
1585                1590                1595                1600
```

-continued

```
Ser Ser Gln Thr Gly Phe Gln Asp Lys Phe Asp Gly Ser Ile Asp Leu
            1605                1610                1615

Gln Ala Asn Trp Tyr Arg Ile Gln Gly Gly Gln Val Asp Ile Asp Cys
    1620                1625                1630

Leu Ser Met Asp Thr Ala Leu Ile Phe Thr Glu Asn Ile Gly Lys Pro
        1635                1640                1645

Arg Tyr Ala Glu Thr Trp Asp Phe His Val Ser Ala Ser Thr Phe Leu
    1650                1655                1660

Gln Phe Glu Met Ser Met Gly Cys Ser Lys Pro Phe Ser Asn Ser His
1665                1670                1675                1680

Ser Val Gln Leu Gln Tyr Ser Leu Asn Asn Gly Lys Asp Trp His Leu
            1685                1690                1695

Val Thr Glu Glu Cys Val Pro Pro Thr Ile Gly Cys Leu His Tyr Thr
        1700                1705                1710

Glu Ser Ser Ile Tyr Thr Ser Glu Arg Phe Gln Asn Trp Lys Arg Ile
            1715                1720                1725

Thr Val Tyr Leu Pro Leu Ser Thr Ile Ser Pro Arg Thr Arg Phe Arg
        1730                1735                1740

Trp Ile Gln Ala Asn Tyr Thr Val Gly Ala Asp Ser Trp Ala Ile Asp
1745                1750                1755                1760

Asn Val Val Leu Ala Ser Gly Cys Pro Trp Met Cys Ser Gly Arg Gly
            1765                1770                1775

Ile Cys Asp Ala Gly Arg Cys Val Cys Asp Arg Gly Phe Gly Gly Pro
        1780                1785                1790

Tyr Cys Val Pro Val Val Pro Leu Pro Ser Ile Leu Lys Asp Asp Phe
    1795                1800                1805

Asn Gly Asn Leu His Pro Asp Leu Trp Pro Glu Val Tyr Gly Ala Glu
    1810                1815                1820

Arg Gly Asn Leu Asn Gly Glu Thr Ile Lys Ser Gly Thr Ser Leu Ile
1825                1830                1835                1840

Phe Lys Gly Glu Gly Leu Arg Met Leu Ile Ser Arg Asp Leu Asp Cys
            1845                1850                1855

Thr Asn Thr Met Tyr Val Gln Phe Ser Leu Arg Phe Ile Ala Lys Ser
        1860                1865                1870

Thr Pro Glu Arg Ser His Ser Ile Leu Leu Gln Phe Ser Ile Ser Gly
        1875                1880                1885

Gly Ile Thr Trp His Leu Met Asp Glu Phe Tyr Phe Pro Gln Thr Thr
    1890                1895                1900

Asn Ile Leu Phe Ile Asn Val Pro Leu Pro Tyr Thr Ala Gln Thr Asn
1905                1910                1915                1920

Ala Thr Arg Phe Arg Leu Trp Gln Pro Tyr Asn Asn Gly Lys Lys Glu
            1925                1930                1935

Glu Ile Trp Ile Val Asp Asp Phe Ile Ile Asp Gly Asn Asn Val Asn
        1940                1945                1950

Asn Pro Val Met Leu Leu Asp Thr Phe Asp Phe Gly Pro Arg Glu Asp
        1955                1960                1965

Asn Trp Phe Phe Tyr Pro Gly Gly Asn Ile Gly Leu Tyr Cys Pro Tyr
    1970                1975                1980

Ser Ser Lys Gly Ala Pro Glu Glu Asp Ser Ala Met Val Phe Val Ser
1985                1990                1995                2000

Asn Glu Val Gly Glu His Ser Ile Thr Thr Arg Asp Leu Asn Val Asn
            2005                2010                2015
```

-continued

Glu Asn Thr Ile Ile Gln Phe Glu Ile Asn Val Gly Cys Ser Thr Asp
        2020                2025                2030

Ser Ser Ser Ala Asp Pro Val Arg Leu Glu Phe Ser Arg Asp Phe Gly
        2035                2040                2045

Ala Thr Trp His Leu Leu Pro Leu Cys Tyr His Ser Ser Ser His
        2050                2055                2060

Val Ser Ser Leu Cys Ser Thr Glu His His Pro Ser Ser Thr Tyr Tyr
2065            2070                2075                2080

Ala Gly Thr Met Gln Gly Trp Arg Arg Glu Val Val His Phe Gly Lys
        2085                2090                2095

Leu His Leu Cys Gly Ser Val Arg Phe Arg Trp Tyr Gln Gly Phe Tyr
        2100                2105                2110

Pro Ala Gly Ser Gln Pro Val Thr Trp Ala Ile Asp Asn Val Tyr Ile
        2115                2120                2125

Gly Pro Gln Cys Glu Glu Met Cys Asn Gly Gln Gly Ser Cys Ile Asn
        2130                2135                2140

Gly Thr Lys Cys Ile Cys Asp Pro Gly Tyr Ser Gly Pro Thr Cys Lys
2145            2150                2155                2160

Ile Ser Thr Lys Asn Pro Asp Phe Leu Lys Asp Asp Phe Glu Gly Gln
        2165                2170                2175

Leu Glu Ser Asp Arg Phe Leu Leu Met Ser Gly Gly Lys Pro Ser Arg
        2180                2185                2190

Lys Cys Gly Ile Leu Ser Ser Gly Asn Asn Leu Phe Phe Asn Glu Asp
        2195                2200                2205

Gly Leu Arg Met Leu Met Thr Arg Asp Leu Asp Leu Ser His Ala Arg
        2210                2215                2220

Phe Val Gln Phe Phe Met Arg Leu Gly Cys Gly Lys Gly Val Pro Asp
2225            2230                2235                2240

Pro Arg Ser Gln Pro Val Leu Leu Gln Tyr Ser Leu Asn Gly Gly Leu
        2245                2250                2255

Ser Trp Ser Leu Leu Gln Glu Phe Leu Phe Ser Asn Ser Ser Asn Val
        2260                2265                2270

Gly Arg Tyr Ile Ala Leu Glu Ile Pro Leu Lys Ala Arg Ser Gly Ser
        2275                2280                2285

Thr Arg Leu Arg Trp Trp Gln Pro Ser Glu Asn Gly His Phe Tyr Ser
        2290                2295                2300

Pro Trp Val Ile Asp Gln Ile Leu Ile Gly Gly Asn Ile Ser Gly Asn
2305            2310                2315                2320

Thr Val Leu Glu Asp Asp Phe Thr Thr Leu Asp Ser Arg Lys Trp Leu
        2325                2330                2335

Leu His Pro Gly Gly Thr Lys Met Pro Val Cys Gly Ser Thr Gly Asp
        2340                2345                2350

Ala Leu Val Phe Ile Glu Lys Ala Ser Thr Arg Tyr Val Val Ser Thr
        2355                2360                2365

Asp Val Ala Val Asn Glu Asp Ser Phe Leu Gln Ile Asp Phe Ala Ala
        2370                2375                2380

Ser Cys Ser Val Thr Asp Ser Cys Tyr Ala Ile Glu Leu Glu Tyr Ser
2385            2390                2395                2400

Val Asp Leu Gly Leu Ser Trp His Pro Leu Val Arg Asp Cys Leu Pro
        2405                2410                2415

Thr Asn Val Glu Cys Ser Arg Tyr His Leu Gln Arg Ile Leu Val Ser
        2420                2425                2430

-continued

```
Asp Thr Phe Asn Lys Trp Thr Arg Ile Thr Leu Pro Leu Pro Pro Tyr
        2435                2440                2445

Thr Arg Ser Gln Ala Thr Arg Phe Arg Trp His Gln Pro Ala Pro Phe
    2450                2455                2460

Asp Lys Gln Gln Thr Trp Ala Ile Asp Asn Val Tyr Ile Gly Asp Gly
2465                2470                2475                2480

Cys Ile Asp Met Cys Ser Gly His Gly Arg Cys Ile Gln Gly Asn Cys
            2485                2490                2495

Val Cys Asp Glu Gln Trp Gly Gly Leu Tyr Cys Asp Pro Glu Thr
            2500                2505                2510

Ser Leu Pro Thr Gln Leu Lys Asp Asn Phe Asn Arg Ala Pro Ser Ser
        2515                2520                2525

Gln Asn Trp Leu Thr Val Asn Gly Gly Lys Leu Ser Thr Val Cys Gly
    2530                2535                2540

Ala Val Ala Ser Gly Met Ala Leu His Phe Ser Gly Gly Cys Ser Arg
2545                2550                2555                2560

Leu Leu Val Thr Val Asp Leu Asn Leu Thr Asn Ala Glu Phe Ile Gln
            2565                2570                2575

Phe Tyr Phe Met Tyr Gly Cys Leu Ile Thr Pro Asn Asn Arg Asn Gln
        2580                2585                2590

Gly Val Leu Leu Glu Tyr Ser Val Asn Gly Gly Ile Thr Trp Asn Leu
    2595                2600                2605

Leu Met Glu Ile Phe Tyr Asp Gln Tyr Ser Lys Pro Gly Phe Val Asn
    2610                2615                2620

Ile Leu Leu Pro Pro Asp Ala Lys Glu Ile Ala Thr Arg Phe Arg Trp
2625                2630                2635                2640

Trp Gln Pro Arg His Asp Gly Leu Asp Gln Asn Asp Trp Ala Ile Asp
            2645                2650                2655

Asn Val Leu Ile Ser Gly Ser Ala Asp Gln Arg Thr Val Met Leu Asp
            2660                2665                2670

Thr Phe Ser Ser Ala Pro Val Pro Gln His Glu Arg Ser Pro Ala Asp
        2675                2680                2685

Ala Gly Pro Val Gly Arg Ile Ala Phe Asp Met Phe Met Glu Asp Lys
    2690                2695                2700

Thr Ser Val Asn Glu His Trp Leu Phe His Asp Asp Cys Thr Val Glu
2705                2710                2715                2720

Arg Phe Cys Asp Ser Pro Asp Gly Val Met Leu Cys Gly Ser His Asp
            2725                2730                2735

Gly Arg Glu Val Tyr Ala Val Thr His Asp Leu Thr Pro Thr Glu Gly
        2740                2745                2750

Trp Ile Met Gln Phe Lys Ile Ser Val Gly Cys Lys Val Ser Glu Lys
        2755                2760                2765

Ile Ala Gln Asn Gln Ile His Val Gln Tyr Ser Thr Asp Phe Gly Val
    2770                2775                2780

Ser Trp Asn Tyr Leu Val Pro Gln Cys Leu Pro Ala Asp Pro Lys Cys
2785                2790                2795                2800

Ser Gly Ser Val Ser Gln Pro Ser Val Phe Pro Thr Lys Gly Trp
            2805                2810                2815

Lys Arg Ile Thr Tyr Pro Leu Pro Glu Ser Leu Val Gly Asn Pro Val
        2820                2825                2830

Arg Phe Arg Phe Tyr Gln Lys Tyr Ser Asp Met Gln Trp Ala Ile Asp
    2835                2840                2845
```

-continued

```
Asn Phe Tyr Leu Gly Pro Gly Cys Leu Asp Asn Cys Arg Gly His Gly
    2850                2855                2860
Asp Cys Leu Arg Glu Gln Cys Ile Cys Asp Pro Gly Tyr Ser Gly Pro
2865                2870                2875                2880
Asn Cys Tyr Leu Thr His Thr Leu Lys Thr Phe Leu Lys Glu Arg Phe
                2885                2890                2895
Asp Ser Glu Glu Ile Lys Pro Asp Leu Trp Met Ser Leu Glu Gly Gly
    2900                2905                2910
Ser Thr Cys Thr Glu Cys Gly Ile Leu Ala Glu Asp Thr Ala Leu Tyr
        2915                2920                2925
Phe Gly Gly Ser Thr Val Arg Gln Ala Val Thr Gln Asp Leu Asp Leu
            2930                2935                2940
Arg Gly Ala Lys Phe Leu Gln Tyr Trp Gly Arg Ile Gly Ser Glu Asn
2945                2950                2955                2960
Asn Met Thr Ser Cys His Arg Pro Ile Cys Arg Lys Glu Gly Val Leu
                2965                2970                2975
Leu Asp Tyr Ser Thr Asp Gly Gly Ile Thr Trp Thr Leu Leu His Glu
    2980                2985                2990
Met Asp Tyr Gln Lys Tyr Ile Ser Val Arg His Asp Tyr Ile Leu Leu
        2995                3000                3005
Pro Glu Asp Ala Leu Thr Asn Thr Thr Arg Leu Arg Trp Trp Gln Pro
            3010                3015                3020
Phe Val Ile Ser Asn Gly Ile Val Ser Gly Val Glu Arg Ala Gln
3025                3030                3035                3040
Trp Ala Leu Asp Asn Ile Leu Ile Gly Gly Ala Glu Ile Asn Pro Ser
                3045                3050                3055
Gln Leu Val Asp Thr Phe Asp Asp Glu Gly Thr Ser His Glu Glu Asn
    3060                3065                3070
Trp Ser Phe Tyr Pro Asn Ala Val Arg Thr Ala Gly Phe Cys Gly Asn
        3075                3080                3085
Pro Ser Phe His Leu Tyr Trp Pro Asn Lys Lys Asp Lys Thr His
            3090                3095                3100
Asn Ala Leu Ser Ser Arg Glu Leu Ile Ile Gln Pro Gly Tyr Met Met
3105                3110                3115                3120
Gln Phe Lys Ile Val Val Gly Cys Glu Ala Thr Ser Cys Gly Asp Leu
                3125                3130                3135
His Ser Val Met Leu Glu Tyr Thr Lys Asp Ala Arg Ser Asp Ser Trp
    3140                3145                3150
Gln Leu Val Gln Thr Gln Cys Leu Pro Ser Ser Asn Ser Ile Gly
        3155                3160                3165
Cys Ser Pro Phe Gln Phe His Glu Ala Thr Ile Tyr Asn Ser Val Asn
            3170                3175                3180
Ser Ser Ser Trp Lys Arg Ile Thr Ile Gln Leu Pro Asp His Val Ser
3185                3190                3195                3200
Ser Ser Ala Thr Gln Phe Arg Trp Ile Gln Lys Gly Glu Glu Thr Glu
                3205                3210                3215
Lys Gln Ser Trp Ala Ile Asp His Val Tyr Ile Gly Glu Ala Cys Pro
    3220                3225                3230
Lys Leu Cys Ser Gly His Gly Tyr Cys Thr Thr Gly Ala Ile Cys Ile
        3235                3240                3245
Cys Asp Glu Ser Phe Gln Gly Asp Asp Cys Ser Val Phe Ser His Asp
            3250                3255                3260
```

```
Leu Pro Ser Tyr Ile Lys Asp Asn Phe Glu Ser Ala Arg Val Thr Glu
3265                3270                3275                3280

Ala Asn Trp Glu Thr Ile Gln Gly Gly Val Ile Gly Ser Gly Cys Gly
            3285                3290                3295

Gln Leu Ala Pro Tyr Ala His Gly Asp Ser Leu Tyr Phe Asn Gly Cys
        3300                3305                3310

Gln Ile Arg Gln Ala Ala Thr Lys Pro Leu Asp Leu Thr Arg Ala Ser
    3315                3320                3325

Lys Ile Met Phe Val Leu Gln Ile Gly Ser Met Ser Gln Thr Asp Ser
3330                3335                3340

Cys Asn Ser Asp Leu Ser Gly Pro His Ala Val Asp Lys Ala Val Leu
3345                3350                3355                3360

Leu Gln Tyr Ser Val Asn Asn Gly Ile Thr Trp His Val Ile Ala Gln
            3365                3370                3375

His Gln Pro Lys Asp Phe Thr Gln Ala Gln Arg Val Ser Tyr Asn Val
        3380                3385                3390

Pro Leu Glu Ala Arg Met Lys Gly Val Leu Arg Trp Trp Gln Pro
    3395                3400                3405

Arg His Asn Gly Thr Gly His Asp Gln Trp Ala Leu Asp His Val Glu
        3410                3415                3420

Val Val Leu Val Ser Thr Arg Lys Gln Asn Tyr Met Met Asn Phe Ser
3425                3430                3435                3440

Arg Gln His Gly Leu Arg His Phe Tyr Asn Arg Arg Arg Ser Leu
            3445                3450                3455

Arg Arg Tyr Pro
            3460

<210> SEQ ID NO 2
<211> LENGTH: 3461
<212> TYPE: PRT
<213> ORGANISM: Mus musculus

<400> SEQUENCE: 2

Met Glu Arg Gly Cys Trp Ala Pro Arg Ala Leu Val Leu Ala Val Leu
1               5                   10                  15

Leu Leu Leu Ala Thr Leu Arg Ala Arg Ala Ala Thr Gly Tyr Tyr Pro
            20                  25                  30

Arg Phe Ser Pro Phe Phe Leu Cys Thr His His Gly Glu Leu Glu
        35                  40                  45

Gly Asp Gly Glu Gln Gly Glu Val Leu Ile Ser Leu His Ile Ala Gly
    50                  55                  60

Asn Pro Thr Tyr Tyr Val Pro Gly Gln Glu Tyr His Val Thr Ile Ser
65                  70                  75                  80

Thr Ser Thr Phe Phe Asp Gly Leu Leu Val Thr Gly Leu Tyr Thr Ser
            85                  90                  95

Thr Ser Ile Gln Ser Ser Gln Ser Ile Gly Gly Ser Ser Ala Phe Gly
        100                 105                 110

Phe Gly Ile Met Ser Asp His Gln Phe Gly Asn Gln Phe Met Cys Ser
    115                 120                 125

Val Val Ala Ser His Val Ser His Leu Pro Thr Thr Asn Leu Ser Phe
130                 135                 140

Val Trp Ile Ala Pro Pro Ala Gly Thr Gly Cys Val Asn Phe Met Ala
145                 150                 155                 160

Thr Ala Thr His Arg Gly Gln Val Ile Phe Lys Asp Ala Leu Ala Gln
            165                 170                 175
```

-continued

```
Gln Leu Cys Glu Gln Gly Ala Pro Thr Glu Ala Thr Ala Tyr Ser His
            180                 185                 190

Leu Ala Glu Ile His Ser Asp Ser Val Ile Leu Arg Asp Asp Phe Asp
            195                 200                 205

Ser Tyr Gln Gln Leu Glu Leu Asn Pro Asn Ile Trp Val Glu Cys Ser
            210                 215                 220

Asn Cys Glu Met Gly Glu Gln Cys Gly Thr Ile Met His Gly Asn Ala
225                 230                 235                 240

Val Thr Phe Cys Glu Pro Tyr Gly Pro Arg Glu Leu Thr Thr Thr Cys
            245                 250                 255

Leu Asn Thr Thr Thr Ala Ser Val Leu Gln Phe Ser Ile Gly Ser Gly
            260                 265                 270

Ser Cys Arg Phe Ser Tyr Ser Asp Pro Ser Ile Thr Val Ser Tyr Ala
            275                 280                 285

Lys Asn Asn Thr Ala Asp Trp Ile Gln Leu Glu Lys Ile Arg Ala Pro
            290                 295                 300

Ser Asn Val Ser Thr Val Ile His Ile Leu Tyr Leu Pro Glu Glu Ala
305                 310                 315                 320

Lys Gly Glu Ser Val Gln Phe Gln Trp Lys Gln Asp Ser Leu Arg Val
            325                 330                 335

Gly Glu Val Tyr Glu Ala Cys Trp Ala Leu Asp Asn Ile Leu Val Ile
            340                 345                 350

Asn Ser Ala His Arg Glu Val Val Leu Glu Asp Asn Leu Asp Pro Val
            355                 360                 365

Asp Thr Gly Asn Trp Leu Phe Phe Pro Gly Ala Thr Val Lys His Ser
            370                 375                 380

Cys Gln Ser Asp Gly Asn Ser Ile Tyr Phe His Gly Asn Glu Gly Ser
385                 390                 395                 400

Glu Phe Asn Phe Ala Thr Thr Arg Asp Val Asp Leu Ser Thr Glu Asp
            405                 410                 415

Ile Gln Glu Gln Trp Ser Glu Glu Phe Glu Ser Gln Pro Thr Gly Trp
            420                 425                 430

Asp Ile Leu Gly Ala Val Val Gly Ala Asp Cys Gly Thr Val Glu Ser
            435                 440                 445

Gly Leu Ser Leu Val Phe Leu Lys Asp Gly Glu Arg Lys Leu Cys Thr
            450                 455                 460

Pro Tyr Met Asp Thr Thr Gly Tyr Gly Asn Leu Arg Phe Tyr Phe Val
465                 470                 475                 480

Met Gly Gly Ile Cys Asp Pro Gly Val Ser His Glu Asn Asp Ile Ile
            485                 490                 495

Leu Tyr Ala Lys Ile Glu Gly Arg Lys Glu His Ile Ala Leu Asp Thr
            500                 505                 510

Leu Thr Tyr Ser Ser Tyr Lys Val Pro Ser Leu Val Ser Val Val Ile
            515                 520                 525

Asn Pro Glu Leu Gln Thr Pro Ala Thr Lys Phe Cys Leu Arg Gln Lys
            530                 535                 540

Ser His Gln Gly Tyr Asn Arg Asn Val Trp Ala Val Asp Phe Phe His
545                 550                 555                 560

Val Leu Pro Val Leu Pro Ser Thr Met Ser His Met Ile Gln Phe Ser
            565                 570                 575

Ile Asn Leu Gly Cys Gly Thr His Gln Pro Gly Asn Ser Val Ser Leu
            580                 585                 590
```

-continued

```
Glu Phe Ser Thr Asn His Gly Arg Ser Trp Ser Leu Leu His Thr Glu
            595                 600                 605

Cys Leu Pro Glu Ile Cys Ala Gly Pro His Leu Pro His Ser Thr Val
        610                 615                 620

Tyr Ser Ser Glu Asn Tyr Ser Gly Trp Asn Arg Ile Thr Ile Pro Leu
625                 630                 635                 640

Pro Asn Ala Ala Leu Thr Arg Asp Thr Arg Ile Arg Trp Arg Gln Thr
                645                 650                 655

Gly Pro Ile Leu Gly Asn Met Trp Ala Ile Asp Asn Val Tyr Ile Gly
            660                 665                 670

Pro Ser Cys Leu Lys Phe Cys Ser Arg Gly Gln Cys Thr Arg His
        675                 680                 685

Gly Cys Lys Cys Asp Pro Gly Phe Ser Gly Pro Ala Cys Glu Met Ala
    690                 695                 700

Ser Gln Thr Phe Pro Met Phe Ile Ser Glu Ser Phe Gly Ser Ala Arg
705                 710                 715                 720

Leu Ser Ser Tyr His Asn Phe Tyr Ser Ile Arg Gly Ala Glu Val Ser
                725                 730                 735

Phe Gly Cys Gly Val Leu Ala Ser Gly Lys Ala Leu Val Phe Asn Lys
            740                 745                 750

Asp Gly Arg Arg Gln Leu Ile Thr Ser Phe Leu Asp Ser Ser Gln Ser
        755                 760                 765

Arg Phe Leu Gln Phe Thr Leu Arg Leu Gly Ser Lys Ser Val Leu Ser
770                 775                 780

Thr Cys Arg Ala Pro Asp Gln Pro Gly Glu Gly Val Leu Leu His Tyr
785                 790                 795                 800

Ser Tyr Asp Asn Gly Ile Thr Trp Lys Leu Leu Glu His Tyr Ser Tyr
                805                 810                 815

Val Asn Tyr His Glu Pro Arg Ile Ile Ser Val Glu Leu Pro Asp Asp
            820                 825                 830

Ala Arg Gln Phe Gly Ile Gln Phe Arg Trp Trp Gln Pro Tyr His Ser
        835                 840                 845

Ser Gln Gly Glu Asp Val Trp Ala Ile Asp Glu Ile Val Met Thr Ser
850                 855                 860

Val Leu Phe Asn Ser Ile Ser Leu Asp Phe Thr Asn Leu Val Glu Val
865                 870                 875                 880

Thr Gln Ser Leu Gly Phe Tyr Leu Gly Asn Val Gln Pro Tyr Cys Gly
                885                 890                 895

His Asp Trp Thr Leu Cys Phe Thr Gly Asp Ser Lys Leu Ala Ser Ser
            900                 905                 910

Met Arg Tyr Val Glu Thr Gln Ser Met Gln Ile Gly Ala Ser Tyr Met
        915                 920                 925

Ile Gln Phe Ser Leu Val Met Gly Cys Gly Gln Lys Tyr Thr Pro His
    930                 935                 940

Met Asp Asn Gln Val Lys Leu Glu Tyr Ser Ala Asn His Gly Leu Thr
945                 950                 955                 960

Trp His Leu Val Gln Glu Glu Cys Leu Pro Ser Met Pro Ser Cys Gln
                965                 970                 975

Glu Phe Thr Ser Ala Ser Ile Tyr His Ala Ser Glu Phe Thr Gln Trp
            980                 985                 990

Arg Arg Val Thr Val Val Leu Pro Gln Lys Thr Trp Ser Gly Ala Thr
        995                 1000                1005
```

-continued

```
Arg Phe Arg Trp Ser Gln Ser Tyr Tyr Thr Ala Gln Asp Glu Trp Ala
    1010                1015                1020
Leu Asp Asn Ile Tyr Ile Gly Gln Gln Cys Pro Asn Met Cys Ser Gly
1025            1030                1035                1040
His Gly Ser Cys Asp His Gly Val Cys Arg Cys Asp Gln Gly Tyr Gln
                1045                1050                1055
Gly Thr Glu Cys His Pro Glu Ala Ala Leu Pro Ser Thr Ile Met Ser
            1060                1065                1070
Asp Phe Glu Asn Pro Ser Ser Trp Glu Ser Asp Trp Gln Glu Val Ile
        1075                1080                1085
Gly Gly Glu Val Val Lys Pro Glu Gln Gly Cys Gly Val Val Ser Ser
    1090                1095                1100
Gly Ser Ser Leu Tyr Phe Ser Lys Ala Gly Lys Arg Gln Leu Val Ser
1105                1110                1115                1120
Trp Asp Leu Asp Thr Ser Trp Val Asp Phe Val Gln Phe Tyr Ile Gln
                1125                1130                1135
Ile Gly Gly Glu Ser Ala Ala Cys Asn Lys Pro Asp Ser Arg Glu Glu
            1140                1145                1150
Gly Ile Leu Leu Gln Tyr Ser Asn Asn Gly Gly Ile Gln Trp His Leu
        1155                1160                1165
Leu Ala Glu Met Tyr Phe Ser Asp Phe Ser Lys Pro Arg Phe Val Tyr
    1170                1175                1180
Leu Glu Leu Pro Ala Ala Gly Lys Thr Pro Cys Thr Arg Phe Arg Trp
1185                1190                1195                1200
Trp Lys Pro Val Phe Ser Gly Glu Asp Tyr Asp Gln Trp Ala Val Asp
                1205                1210                1215
Asp Ile Ile Ile Leu Ser Glu Lys Gln Lys Gln Val Ile Pro Val Val
            1220                1225                1230
Asn Pro Thr Leu Pro Gln Asn Phe Tyr Glu Lys Pro Ala Phe Asp Tyr
        1235                1240                1245
Pro Met Asn Gln Met Ser Val Trp Leu Met Leu Ala Asn Glu Gly Met
    1250                1255                1260
Ala Lys Asn Asp Ser Phe Cys Ala Thr Thr Pro Ser Ala Met Val Phe
1265                1270                1275                1280
Gly Lys Ser Asp Gly Asp Arg Phe Ala Val Thr Arg Asp Leu Thr Leu
                1285                1290                1295
Lys Pro Gly Tyr Val Leu Gln Phe Lys Leu Asn Ile Gly Cys Thr Ser
            1300                1305                1310
Gln Phe Ser Ser Thr Ala Pro Val Leu Leu Gln Tyr Ser His Asp Ala
        1315                1320                1325
Gly Met Ser Trp Phe Leu Leu Lys Glu Gly Cys Phe Pro Ala Ser Ala
    1330                1335                1340
Ala Lys Gly Cys Glu Gly Asn Ser Arg Glu Leu Ser Glu Pro Thr Val
1345                1350                1355                1360
Tyr Tyr Thr Gly Asp Phe Glu Glu Trp Thr Arg Ile Thr Ile Ala Ile
                1365                1370                1375
Pro Arg Ser Leu Ala Ser Ser Lys Thr Arg Phe Arg Trp Ile Gln Glu
            1380                1385                1390
Ser Ser Ser Gln Lys Asn Val Pro Pro Phe Gly Leu Asp Gly Val Tyr
        1395                1400                1405
Ile Ser Glu Pro Cys Pro Ser Tyr Cys Ser Gly His Gly Asp Cys Ile
    1410                1415                1420
```

```
Ser Gly Val Cys Phe Cys Asp Leu Gly Tyr Thr Ala Ala Gln Gly Thr
1425                1430                1435                1440

Cys Val Ser Asn Thr Pro Asn His Ser Glu Met Phe Asp Arg Phe Glu
                1445                1450                1455

Gly Lys Leu Ser Pro Leu Trp Tyr Lys Ile Thr Gly Gly Gln Val Gly
                1460                1465                1470

Thr Gly Cys Gly Thr Leu Asn Asp Gly Arg Ser Leu Tyr Phe Asn Gly
                1475                1480                1485

Leu Gly Lys Arg Glu Ala Arg Thr Val Pro Leu Asp Thr Arg Asn Ile
                1490                1495                1500

Ser Leu Val Gln Phe Tyr Ile Gln Ile Gly Ser Lys Thr Ser Gly Ile
1505                1510                1515                1520

Thr Tyr Ile Thr Pro Arg Ala Arg Tyr Glu Gly Leu Val Val Gln Tyr
                1525                1530                1535

Ser Asn Asp Asn Gly Ile Leu Trp His Leu Leu Arg Glu Leu Asp Phe
                1540                1545                1550

Met Ser Phe Leu Glu Pro Gln Ile Ile Ser Ile Asp Leu Pro Arg Glu
                1555                1560                1565

Ala Lys Thr Pro Ala Thr Ala Phe Arg Trp Trp Gln Pro Gln His Gly
1570                1575                1580

Lys His Ser Ala Gln Trp Ala Leu Gly Asp Val Leu Ile Gly Val Asn
1585                1590                1595                1600

Asp Ser Ser Gln Thr Gly Phe Gln Asp Lys Leu Asp Gly Ser Ile Asp
                1605                1610                1615

Leu Gln Ala Asn Trp Tyr Arg Ile Gln Gly Gly Gln Val Asp Ile Asp
                1620                1625                1630

Cys Leu Ser Met Asp Thr Ala Leu Ile Phe Thr Glu Asn Ile Gly Asn
1635                1640                1645

Pro Arg Tyr Ala Glu Thr Trp Asp Phe His Val Ser Glu Ser Ser Phe
                1650                1655                1660

Leu Gln Trp Glu Met Asn Met Gly Cys Ser Lys Pro Phe Ser Gly Ala
1665                1670                1675                1680

His Gly Ile Gln Leu Gln Tyr Ser Leu Asn Asn Gly Lys Asp Trp Gln
                1685                1690                1695

Leu Val Thr Glu Glu Cys Val Pro Pro Thr Ile Gly Cys Val His Tyr
                1700                1705                1710

Thr Glu Ser Ser Thr Tyr Thr Ser Glu Arg Phe Gln Asn Trp Arg Arg
                1715                1720                1725

Val Thr Val Tyr Leu Pro Leu Ala Thr Asn Ser Pro Arg Thr Arg Phe
                1730                1735                1740

Arg Trp Ile Gln Thr Asn Tyr Thr Val Gly Ala Asp Ser Trp Ala Ile
1745                1750                1755                1760

Asp Asn Val Ile Leu Ala Ser Gly Cys Pro Trp Met Cys Ser Gly Arg
                1765                1770                1775

Gly Ile Cys Asp Ser Gly Arg Cys Val Cys Asp Arg Gly Phe Gly Gly
                1780                1785                1790

Pro Phe Cys Val Pro Val Val Pro Leu Pro Ser Ile Leu Lys Asp Asp
                1795                1800                1805

Phe Asn Gly Asn Leu His Pro Asp Leu Trp Pro Glu Val Tyr Gly Ala
                1810                1815                1820

Glu Arg Gly Asn Leu Asn Gly Glu Thr Ile Lys Ser Gly Thr Cys Leu
1825                1830                1835                1840
```

```
Ile Phe Lys Gly Glu Gly Leu Arg Met Leu Ile Ser Arg Asp Leu Asp
            1845                1850                1855

Cys Thr Asn Thr Met Tyr Val Gln Phe Ser Leu Arg Phe Ile Ala Lys
            1860                1865                1870

Gly Thr Pro Glu Arg Ser His Ser Ile Leu Leu Gln Phe Ser Val Ser
            1875                1880                1885

Gly Gly Val Thr Trp His Leu Met Asp Glu Phe Tyr Phe Pro Gln Thr
            1890                1895                1900

Thr Ser Ile Leu Phe Ile Asn Val Pro Leu Pro Tyr Gly Ala Gln Thr
1905                1910                1915                1920

Asn Ala Thr Arg Phe Arg Leu Trp Gln Pro Tyr Asn Asn Gly Lys Lys
            1925                1930                1935

Glu Glu Ile Trp Ile Ile Asp Asp Phe Ile Asp Gly Asn Asn Leu
            1940                1945                1950

Asn Asn Pro Val Leu Leu Leu Asp Thr Phe Asp Phe Gly Pro Arg Glu
            1955                1960                1965

Asp Asn Trp Phe Phe Tyr Pro Gly Gly Asn Ile Gly Leu Tyr Cys Pro
            1970                1975                1980

Tyr Ser Ser Lys Gly Ala Pro Glu Glu Asp Ser Ala Met Val Phe Val
1985                1990                1995                2000

Ser Asn Glu Val Gly Glu His Ser Ile Thr Thr Arg Asp Leu Ser Val
            2005                2010                2015

Asn Glu Asn Thr Ile Ile Gln Phe Glu Ile Asn Val Gly Cys Ser Thr
            2020                2025                2030

Asp Ser Ser Ser Ala Asp Pro Val Arg Leu Glu Phe Ser Arg Asp Phe
            2035                2040                2045

Gly Ala Thr Trp His Leu Leu Leu Pro Leu Cys Tyr His Ser Ser Ser
            2050                2055                2060

Leu Val Ser Ser Leu Cys Ser Thr Glu His His Pro Ser Ser Thr Tyr
2065                2070                2075                2080

Tyr Ala Gly Thr Thr Gln Gly Trp Arg Arg Glu Val Val His Phe Gly
            2085                2090                2095

Lys Leu His Leu Cys Gly Ser Val Arg Phe Arg Trp Tyr Gln Gly Phe
            2100                2105                2110

Tyr Pro Ala Gly Ser Gln Pro Val Thr Trp Ala Ile Asp Asn Val Tyr
            2115                2120                2125

Ile Gly Pro Gln Cys Glu Glu Met Cys Tyr Gly His Gly Ser Cys Ile
            2130                2135                2140

Asn Gly Thr Lys Cys Ile Cys Asp Pro Gly Tyr Ser Gly Pro Thr Cys
2145                2150                2155                2160

Lys Ile Ser Thr Lys Asn Pro Asp Phe Leu Lys Asp Asp Phe Glu Gly
            2165                2170                2175

Gln Leu Glu Ser Asp Arg Phe Leu Leu Met Ser Gly Gly Lys Pro Ser
            2180                2185                2190

Arg Lys Cys Gly Ile Leu Ser Ser Gly Asn Asn Leu Phe Phe Asn Glu
            2195                2200                2205

Asp Gly Leu Arg Met Leu Val Thr Arg Asp Leu Asp Leu Ser His Ala
            2210                2215                2220

Arg Phe Val Gln Phe Phe Met Arg Leu Gly Cys Gly Lys Gly Val Pro
2225                2230                2235                2240

Asp Pro Arg Ser Gln Pro Val Leu Leu Gln Tyr Ser Leu Asn Gly Gly
            2245                2250                2255
```

-continued

```
Leu Ser Trp Ser Leu Leu Gln Glu Phe Leu Phe Ser Asn Ser Ser Asn
            2260                2265                2270

Val Gly Arg Tyr Ile Ala Leu Glu Met Pro Leu Lys Ala Arg Ser Gly
        2275                2280                2285

Ser Thr Arg Leu Arg Trp Trp Gln Pro Ser Glu Asn Gly His Phe Tyr
    2290                2295                2300

Ser Pro Trp Val Ile Asp Gln Ile Leu Ile Gly Gly Asn Ile Ser Gly
2305                2310                2315                2320

Asn Thr Val Leu Glu Asp Asp Phe Ser Thr Leu Asp Ser Arg Lys Trp
                2325                2330                2335

Leu Leu His Pro Gly Gly Thr Lys Met Pro Val Cys Gly Ser Thr Gly
            2340                2345                2350

Asp Ala Leu Val Phe Ile Glu Lys Ala Ser Thr Arg Tyr Val Val Thr
        2355                2360                2365

Thr Asp Ile Ala Val Asn Glu Asp Ser Phe Leu Gln Ile Asp Phe Ala
    2370                2375                2380

Ala Ser Cys Ser Val Thr Asp Ser Cys Tyr Ala Ile Glu Leu Glu Tyr
2385                2390                2395                2400

Ser Val Asp Leu Gly Leu Ser Trp His Pro Leu Val Arg Asp Cys Leu
                2405                2410                2415

Pro Thr Asn Val Glu Cys Ser Arg Tyr His Leu Gln Arg Ile Leu Val
            2420                2425                2430

Ser Asp Thr Phe Asn Lys Trp Thr Arg Ile Thr Leu Pro Leu Pro Ser
        2435                2440                2445

Tyr Thr Arg Ser Gln Ala Thr Arg Phe Arg Trp His Gln Pro Ala Pro
    2450                2455                2460

Phe Asp Lys Gln Gln Thr Trp Ala Ile Asp Asn Val Tyr Ile Gly Asp
2465                2470                2475                2480

Gly Cys Leu Asp Met Cys Ser Gly His Gly Arg Cys Val Gln Gly Ser
                2485                2490                2495

Cys Val Cys Asp Glu Gln Trp Gly Gly Leu Tyr Cys Asp Glu Pro Glu
            2500                2505                2510

Thr Ser Leu Pro Thr Gln Leu Lys Asp Asn Phe Asn Arg Ala Pro Ser
        2515                2520                2525

Asn Gln Asn Trp Leu Thr Val Ser Gly Gly Lys Leu Ser Thr Val Cys
    2530                2535                2540

Gly Ala Val Ala Ser Gly Leu Ala Leu His Phe Ser Gly Gly Cys Ser
2545                2550                2555                2560

Arg Leu Leu Val Thr Val Asp Leu Asn Leu Thr Asn Ala Glu Phe Ile
                2565                2570                2575

Gln Phe Tyr Phe Met Tyr Gly Cys Leu Ile Thr Pro Ser Asn Arg Asn
            2580                2585                2590

Gln Gly Val Leu Leu Glu Tyr Ser Val Asn Gly Gly Ile Thr Trp Asn
        2595                2600                2605

Leu Leu Met Glu Ile Phe Tyr Asp Gln Tyr Ser Lys Pro Gly Phe Val
    2610                2615                2620

Asn Ile Leu Leu Pro Pro Asp Ala Lys Glu Ile Ala Thr Arg Phe Arg
2625                2630                2635                2640

Trp Trp Gln Pro Arg His Asp Gly Leu Asp Gln Asn Asp Trp Ala Ile
                2645                2650                2655

Asp Asn Val Leu Ile Ser Gly Ser Ala Asp Gln Arg Thr Val Met Leu
            2660                2665                2670
```

-continued

```
Asp Thr Phe Ser Ser Ala Pro Val Pro Gln His Glu Arg Ser Pro Ala
        2675                2680                2685

Asp Ala Gly Pro Val Gly Arg Ile Ala Phe Glu Met Phe Leu Glu Asp
        2690                2695                2700

Lys Thr Ser Val Asn Glu Asn Trp Leu Phe His Asp Asp Cys Thr Val
2705                2710                2715                2720

Glu Arg Phe Cys Asp Ser Pro Asp Gly Val Met Leu Cys Gly Ser His
            2725                2730                2735

Asp Gly Arg Glu Val Tyr Ala Val Thr His Asp Leu Thr Pro Thr Glu
            2740                2745                2750

Asn Trp Ile Met Gln Phe Lys Ile Ser Val Gly Cys Lys Val Pro Glu
            2755                2760                2765

Lys Ile Ala Gln Asn Gln Ile His Val Gln Phe Ser Thr Asp Phe Gly
        2770                2775                2780

Val Ser Trp Ser Tyr Leu Val Pro Gln Cys Leu Pro Ala Asp Pro Lys
2785                2790                2795                2800

Cys Ser Gly Ser Val Ser Gln Pro Ser Val Phe Phe Pro Thr Glu Gly
            2805                2810                2815

Trp Lys Arg Ile Thr Tyr Pro Leu Pro Glu Ser Leu Thr Gly Asn Pro
            2820                2825                2830

Val Arg Phe Arg Phe Tyr Gln Lys Tyr Ser Asp Val Gln Trp Ala Ile
        2835                2840                2845

Asp Asn Phe Tyr Leu Gly Pro Gly Cys Leu Asp Asn Cys Gly Gly His
        2850                2855                2860

Gly Asp Cys Leu Lys Glu Gln Cys Ile Cys Asp Pro Gly Tyr Ser Gly
2865                2870                2875                2880

Pro Asn Cys Tyr Leu Thr His Ser Leu Lys Thr Phe Leu Lys Glu Arg
            2885                2890                2895

Phe Asp Ser Glu Glu Ile Lys Pro Asp Leu Trp Met Ser Leu Glu Gly
            2900                2905                2910

Gly Ser Thr Cys Thr Glu Cys Gly Val Leu Ala Glu Asn Thr Ala Leu
        2915                2920                2925

Tyr Phe Gly Gly Ser Thr Val Arg Gln Ala Ile Thr Gln Asp Leu Asp
        2930                2935                2940

Leu Arg Gly Ala Lys Phe Leu Gln Tyr Trp Gly Arg Ile Gly Ser Glu
2945                2950                2955                2960

Asn Asn Met Thr Ser Cys His Arg Pro Val Cys Arg Lys Glu Gly Val
            2965                2970                2975

Leu Leu Asp Phe Ser Thr Asp Gly Gly Ile Thr Trp Thr Leu Leu His
            2980                2985                2990

Glu Met Asp Phe Gln Lys Tyr Ile Ser Val Arg His Asp Tyr Ile Leu
            2995                3000                3005

Leu Pro Glu Gly Ala Leu Thr Asn Thr Thr Arg Leu Arg Trp Trp Gln
        3010                3015                3020

Pro Phe Val Ile Ser Asn Gly Leu Val Val Ser Gly Val Glu Arg Ala
3025                3030                3035                3040

Gln Trp Ala Leu Asp Asn Ile Leu Ile Gly Gly Ala Glu Ile Asn Pro
            3045                3050                3055

Ser Gln Leu Val Asp Thr Phe Asp Asp Glu Gly Ser Ser His Glu Glu
            3060                3065                3070

Asn Trp Ser Phe Tyr Pro Asn Ala Val Arg Thr Ala Gly Phe Cys Gly
            3075                3080                3085
```

-continued

```
Asn Pro Ser Phe His Leu Tyr Trp Pro Asn Lys Lys Asp Lys Thr
    3090                3095                3100

His Asn Ala Leu Ser Ser Arg Glu Leu Ile Ile Gln Pro Gly Tyr Met
3105            3110                3115                3120

Met Gln Phe Lys Ile Val Val Gly Cys Glu Ala Thr Ser Cys Gly Asp
                3125                3130                3135

Leu His Ser Val Met Leu Glu Tyr Thr Lys Asp Ala Arg Ser Asp Ser
            3140                3145                3150

Trp Gln Leu Val Gln Thr Gln Cys Leu Pro Ser Ser Ser Asn Ser Ile
        3155                3160                3165

Gly Cys Ser Pro Phe Gln Phe His Glu Ala Thr Ile Tyr Asn Ala Val
    3170                3175                3180

Asn Ser Ser Ser Trp Lys Arg Ile Thr Ile Gln Leu Pro Asp His Val
3185            3190                3195                3200

Ser Ser Ser Ala Thr Gln Phe Arg Trp Ile Gln Lys Gly Glu Thr
                3205                3210                3215

Glu Lys Gln Ser Trp Ala Ile Asp His Val Tyr Ile Gly Glu Ala Cys
            3220                3225                3230

Pro Lys Leu Cys Ser Gly His Gly Tyr Cys Thr Thr Gly Ala Val Cys
        3235                3240                3245

Ile Cys Asp Glu Ser Phe Gln Gly Asp Asp Cys Ser Val Phe Ser His
    3250                3255                3260

Glu Leu Pro Ser Tyr Ile Lys Asp Asn Phe Glu Ser Ala Arg Val Thr
3265            3270                3275                3280

Glu Ala Asn Trp Glu Thr Ile Gln Gly Gly Val Ile Gly Ser Gly Cys
                3285                3290                3295

Gly Gln Leu Ala Pro Tyr Ala His Gly Asp Ser Leu Tyr Phe Asn Gly
            3300                3305                3310

Cys Gln Ile Arg Gln Ala Ala Thr Lys Pro Leu Asp Leu Thr Arg Ala
        3315                3320                3325

Ser Lys Ile Met Phe Val Leu Gln Ile Gly Ser Pro Ala Gln Thr Asp
    3330                3335                3340

Ser Cys Asn Ser Asp Leu Ser Gly Pro His Thr Val Asp Lys Ala Val
3345            3350                3355                3360

Leu Leu Gln Tyr Ser Val Asn Asn Gly Ile Thr Trp His Val Ile Ala
                3365                3370                3375

Gln His Gln Pro Lys Asp Phe Thr Gln Ala Gln Arg Val Ser Tyr Asn
            3380                3385                3390

Val Pro Leu Glu Ala Arg Met Lys Gly Val Leu Leu Arg Trp Trp Gln
        3395                3400                3405

Pro Arg His Asn Gly Thr Gly His Asp Gln Trp Ala Leu Asp His Val
    3410                3415                3420

Glu Val Val Leu Val Ser Thr Arg Lys Gln Asn Tyr Met Met Asn Phe
3425            3430                3435                3440

Ser Arg Gln His Gly Leu Arg His Phe Tyr Asn Arg Arg Arg Ser
                3445                3450                3455

Leu Arg Arg Tyr Pro
            3460

<210> SEQ ID NO 3
<211> LENGTH: 11673
<212> TYPE: DNA
<213> ORGANISM: Mus musculus
```

<400> SEQUENCE: 3

```
ggggcgtcgc gtgcacaccg gcggcggcgg cgctcggagg cggacgacgc gctctcggcg      60
cccgcggccc cggttccccc cgcgctctcg ctccggcggc ccaaagtaac ttcgggagcc     120
tcggtctccc gctaacttcc ccccgcgggc tcggttgccc ggacccgctc ggctcgagcc     180
cgccgccggc tcgccttccc cgcacgcggc tcctccgtgc cggtgcctcc gaaagtggat     240
gagagagcgc gcggggcgcg cggcggcacg gagcgcggcg gcatggagcg cggctgctgg     300
gcgccgcggg ctctcgtcct ggccgtgctg ctgctgctgg cgacgctgag ggcgcgcgcg     360
gccaccggct actacccgcg cttctcgcct ttcttttttcc tgtgcaccca ccacggggag     420
ctggaagggg atggggagca gggcgaggtg ctcatttccc tgcacattgc gggcaacccc     480
acctactacg taccgggaca ggaataccat gttacaattt caacaagcac cttctttgat     540
ggcttgctgg tgacgggact ctatacctcg acaagcatcc agtcttctca gagcattgga     600
ggctccagcg cctttggatt cgggatcatg tccgaccacc agtttggtaa ccagtttatg     660
tgcagtgtgg tggcctctca tgtgagtcac ctgcctacaa ccaacctcag ctttgtctgg     720
attgccccac cagctggcac aggctgtgtg aatttcatgg ctactgcaac atagggggc     780
caggtgattt tcaaagacgc actggcccag cagctgtgtg aacaaggagc tcccacagag     840
gccactgctt actcgcacct tgctgaaata cacagtgaca gtgtgatcct acgagatgac     900
tttgactcct accagcaact ggaattgaac cccaacatat gggttgaatg cagcaactgt     960
gagatgggag agcagtgtgg caccatcatg catggcaatg ctgtcacctt ctgtgagccg    1020
tacggccctc gagagctgac caccacatgc ctgaacacaa caacagcatc tgtcctccag    1080
ttttccattg ggtcaggatc atgtcgattt agttactctg accccagcat cactgtgtca    1140
tacgccaaga caataccgc tgattggatt cagctggaga aaattagagc cccttccaat    1200
gtgagcacag tcatccacat cctgtacctc cccgaggaag ccaaagggga gagcgtgcag    1260
ttccagtgga acaggacag cctgcgagtg ggtgaggtgt atgaggcctg ctgggccctg    1320
gataacatcc tggtcatcaa ttcagcccac agagaagtcg ttctggagga caacctcgac    1380
ccggtcgaca cgggcaactg gctcttcttc cctggagcaa cggtcaagca tagctgtcag    1440
tcagatggga actccattta tttccatgga aatgaaggca gcgagttcaa ttttgccacc    1500
acccgggatg tagatctttc tacagaggat attcaagagc agtggtcaga agaatttgag    1560
agccagccca caggatggga tatcttggga gcagtagttg gtgcagactg tggaaccgta    1620
gaatcaggac tatcactggt gttcctcaaa gatggagaga ggaagctttg cacccccctac    1680
atggatacaa ctggttatgg caacctgagg ttctacttcg ttatgggagg aatctgtgac    1740
cctggagtct ctcatgaaaa cgatatcatc ttatatgcaa agattgaagg aagaaaagaa    1800
cacattgcac tggacactct tacctattct tcctataagg ttccgtctt ggtttctgtg    1860
gtcatcaacc ctgaacttca gacacctgcc accaaattt gtctcaggca aaagagccac    1920
caagggtata atcggaatgt ctgggctgtg gacttcttcc atgtgctgcc cgttctccct    1980
tcaacaatgt ctcacatgat ccagtttttct attaatttgg gatgcggcac acaccagcct    2040
gggaacagcg tcagcttgga gttttctact aaccatggac ggtcctggtc cctactccac    2100
actgagtgct tgccggagat ctgtgcaggc ccccacctcc cccacagcac tgtctactcc    2160
tcagaaaact acagcgggtg gaaccgaatc acgattcctc tccctaatgc agcactcacc    2220
cgagacacca ggattcgctg gagacaaaca ggcccaatcc tgggaaatat gtgggcaatt    2280
gataatgttt atataggtcc ttcgtgtctc aaattctgtt ctggcagagg acaatgcact    2340
```

-continued

```
cggcatggct gcaagtgtga cccaggattt tctggcccag cttgtgagat ggcatctcag    2400
acattcccaa tgtttatttc ggaaagcttt ggcagtgcca gactttcctc ttaccataac    2460
ttttactcta tccgtggtgc tgaagtcagc tttggttgtg gtgtcttagc cagtggtaag    2520
gctctggttt tcaacaaaga tgggaggcgg cagctaatca cgtcctttct ggacagctcg    2580
cagtccaggt ttcttcagtt tacactgagg ctggggagca agtctgtgct gagcacgtgc    2640
agagcccctg accagccggg ggagggagtc ctgctgcact attcatatga caacgggata    2700
acatggaaac tcctggagca ctattcctac gtcaactacc acgagcccag aataatctct    2760
gtagagctac cggatgatgc aagacagttt ggaatccagt tcagatggtg gcagccttac    2820
cattcttccc aaggagaaga cgtgtgggcc attgatgaga ttgtcatgac ctcagtcctg    2880
ttcaacagca tcagtctcga ctttaccaat cttgtggaag tcactcaatc cctgggattc    2940
taccttggca atgttcaacc atactgtggc catgactgga cgctttgttt tacgggagat    3000
tctaaacttg cctcaagcat gcgctatgtg gaaacacagt ccatgcagat cggagcatcc    3060
tatatgattc agttcagcct agtgatggga tgtggccaga aatacactcc tcacatggac    3120
aaccaggtga agctggagta ctcagccaac cacggcctta catggcacct tgtacaagaa    3180
gaatgccttc ccagtatgcc aagctgccag gaatttacat ctgccagcat ttaccatgcc    3240
agcgagttca cacagtggag aagagtcact gttgttcttc cccagaaaac atggtccggt    3300
gccacccgct tccgttggag tcagagctat tacacagccc aggatgagtg ggctttagac    3360
aacatttaca ttgggcagca gtgccccaac atgtgcagtg gcatggctc atgtgaccat    3420
ggcgtgtgca ggtgtgacca gggataccag ggcactgaat gccacccaga agctgcactt    3480
ccttccacga ttatgtcaga ttttgagaac ccgagcagtt gggaatcaga ctggcaggaa    3540
gttattgggg gagaagttgt aaagcctgag caaggctgtg gagtcgtgtc ttctggatct    3600
tctctgtact tcagcaaggc tgggaagagg cagctggtga gctgggacct ggacacatcc    3660
tgggtggact ttgtccagtt ctacatccag ataggaggag agagtgctgc atgcaacaag    3720
cctgacagca gagaggaggg cattctgctc cagtatagca caacggggg catccagtgg    3780
cacctgctgg cagagatgta cttctcagac ttcagcaaac ccagatttgt ctacctggag    3840
ctcccagctg ctgggaagac cccttgtacc aggttccgct ggtggaagcc tgtgttctcg    3900
ggggaggact atgaccagtg ggccgttgat gatatcatca ttctgtcaga gaagcagaag    3960
caggttatcc cagttgtcaa cccaactttg ccccagaact tctatgagaa gccagctttc    4020
gattacccta tgaaccaaat gagtgtgtgg ctaatgttgg ccaatgaagg catggctaaa    4080
aacgacagct ctgtgcgac cacgccgtca gccatggtgt ttggaaagtc agatggagac    4140
cggtttgcag taactcgaga tctgaccctg aaacctggat atgtgctgca gttcaagcta    4200
aacataggct gcaccagcca gttcagcagc actgccccgg ttctcctgca gtattcacat    4260
gatgccggca tgtcgtggtt tctgttgaag gaaggatgct tcccagcgtc agcagccaaa    4320
ggatgtgaag gaactccag ggaattgagt gagcctactg tctattatac tggggacttc    4380
gaagaatgga ctagaatcac cattgccatt ccaaggtccc ttgcatccag caagaccaga    4440
ttccgatgga tccaagagag cagctctcag aagaatgtgc cccgtttgg cttagatggg    4500
gtgtacatat ctgagccttg tcccagttac tgcagtggcc atggagactg catctcgggg    4560
gtgtgtttt gtgacctggg gtacacagct gcacaaggaa cctgtgtgtc aaacaccct    4620
aaccacagtg agatgttcga caggttgag gggaagctaa gcccactgtg gtacaaaatc    4680
accgggggtc aggttggcac gggctgtggc accctcaatg acggcaggtc cctctacttt    4740
```

-continued

| | | | | |
|---|---|---|---|---|
| aatggccttg | ggaaaaggga | agccaggaca | gtcccactgg | acaccaggaa tatcagtctt | 4800 |
| gttcagtttt | atatacaaat | tggaagtaaa | acatcaggga | ttacgtacat caccccacgg | 4860 |
| gctagatatg | agggcttgt | tgttcagtat | tccaatgata | atgggatact ttggcatttg | 4920 |
| ctgagagagt | tggatttcat | gtcattcctg | agccacaga | tcatttccat tgacctgccc | 4980 |
| cgggaagcaa | agacacctgc | cacagctttc | cggtggtggc | agccgcagca tgggaagcat | 5040 |
| tcggcccagt | gggctttggg | tgatgtcctt | ataggagtga | atgacagctc tcaaactgga | 5100 |
| tttcaagata | aattggatgg | ctccatagac | ttgcaagcca | actggtatcg aatccaggga | 5160 |
| ggccaagttg | atatcgactg | cctctctatg | acactgccc | ttatattcac tgaaaacata | 5220 |
| ggaaaccctc | gctatgctga | gacctgggac | ttccatgtgt | cagagtcaag cttcttacag | 5280 |
| tgggaaatga | acatgggctg | cagcaagcct | ttcagtggtg | cccacggcat acagctccag | 5340 |
| tactctctga | acaacggcaa | ggactggcag | cttgtcaccg | aagagtgtgt ccctccaacc | 5400 |
| attgggtgcg | tgcactacac | agagagttca | acttacacat | cagaaagatt ccagaactgg | 5460 |
| aggcgggtca | cggtctacct | gccactcgcc | accaattctc | ccaggactcg gttcagatgg | 5520 |
| attcagacca | actatactgt | tggagcagat | tcctgggcta | ttgataatgt catcctggcc | 5580 |
| tcgggctgtc | cttggatgtg | ctcaggacga | gggatctgtg | attcggggcg ctgtgtgtgt | 5640 |
| gaccggggct | tcggtggacc | cttctgtgtt | cctgttgttc | ctcttccctc cattctaaaa | 5700 |
| gatgatttca | atgggaactt | acatcctgac | ctttggcctg | aagtgtacgg ggcagagagg | 5760 |
| ggcaatctga | atgcgaaac | catcaaatcc | ggaacatgtc | tgatctttaa aggggaggga | 5820 |
| ctaagaatgc | ttatttccag | agatctagat | tgtaccaata | ctatgtatgt ccagttctct | 5880 |
| ctccgattta | tagcgaaagg | taccccagag | aggtctcact | ccatccttct acagttctct | 5940 |
| gtcagtggag | gagtcacctg | gcacctgatg | gatgaattct | acttccctca aacgaccagc | 6000 |
| atactttca | tcaatgttcc | cttaccatac | ggtgcccaaa | ccaacgctac aagattcaga | 6060 |
| ctctggcaac | cgtacaataa | tggtaagaaa | gaagaaatct | ggatcattga tgactttatt | 6120 |
| attgatggaa | acaatttgaa | caaccccgtg | ctgctgctgg | acacgttcga ctttgggccc | 6180 |
| agggaagaca | attggttttt | ctatccgggt | ggtaatatcg | actttactg cccgtattct | 6240 |
| tcaaaggag | ctcctgagga | ggattcggcc | atggtgtttg | tttcaaacga agttggagaa | 6300 |
| cactccatta | ccacacgaga | cctaagtgtg | aacgagaaca | ccatcattca atttgagatc | 6360 |
| aatgttggct | gctccactga | tagttcttct | gctgatccgg | tcagactgga attctcaagg | 6420 |
| gactttggag | ccacctggca | cctgctgctg | cctctctgct | accacagcag cagcctcgtc | 6480 |
| agctccttat | gctccactga | gcatcacccg | agcagcacct | actacgcggg gaccacccag | 6540 |
| ggctggcggc | gggaggtcgt | gcacttcgga | aagctgcacc | tttgtggatc tgtgcgtttc | 6600 |
| cgttggtacc | aggattttta | tcctgctggc | tctcagccgg | tcacatgggc cattgacaat | 6660 |
| gtctacattg | gtccccagtg | tgaagagatg | tgctatgggc | acgggagctg catcaatgga | 6720 |
| accaagtgta | tatgtgaccc | gggctactct | gggccaacct | gtaaaataag caccaaaaat | 6780 |
| cctgattttc | tcaaagacga | ctttgaaggt | caactggaat | ccgatcgatt cttactgatg | 6840 |
| agcggtggga | agccgtctcg | taagtgtggc | atccttttcca | gtgggaacaa cctcttcttc | 6900 |
| aatgaggacg | gcttgcgcat | gctagtaaca | cgggacctgg | atttatcaca tgcaaggttt | 6960 |
| gtgcagttct | tcatgagact | gggatgtggt | aaagtgttc | cagacccag gagccagccc | 7020 |
| gtgcttctgc | agtactccct | caatggcggc | ctctcctgga | gtcttcttca agagttcctc | 7080 |
| ttcagcaact | ccagcaatgt | gggcaggtac | attgccctgg | aaatgcccct gaaagcccgt | 7140 |

```
tctggttcga cacgcctccg ctggtggcag ccatctgaaa atgggcactt ctatagcccc    7200
tgggtgatcg accagattct tattggagga aatatctctg gtaatacagt cttagaagat    7260
gatttctcaa ctctggacag cagaaagtgg ctgcttcacc caggaggcac caagatgcct    7320
gtgtgtggct ccacaggcga tgccctggtc tttattgaaa aggccagcac ccgttacgtg    7380
gtcacgacag acatcgctgt gaatgaggac tcattcctac agatagactt tgctgcctcc    7440
tgctcagtca cagactcctg ctatgctatt gaactggagt actcggtgga tctcggtctg    7500
tcgtggcacc cgctggtgag ggactgcctg cctaccaatg ttgagtgtag tcgttaccac    7560
ctgcagcgga tcctggtgtc agatactttc aacaagtgga ccagaatcac tctgcccctg    7620
ccttcctaca ccaggtctca agccactcgt ttccgctggc atcagccagc gccttttgac    7680
aagcagcaga cctgggcaat agataatgtc tatattgggg atggttgcct agacatgtgc    7740
agtggccacg ggagatgcgt ccagggaagc tgtgtctgtg atgaacagtg gggaggcctg    7800
tactgtgatg agcctgagac ctcccttccc acccagctca agacaacttt caaccgagcc    7860
ccctccaacc agaactggct gactgtgagc ggtgggaagc tgagtacagt gtgtgggct    7920 gtggcttccg gcctggctct ccatttcagt gggggctgca gccgattgtt agtcactgtg    7980
gatctgaacc tcaccaatgc tgagtttatc cagtttttact ttatgtatgg atgcctcatt    8040
acgccgagca accgtaacca gggagtcctg ctggagtact ctgtcaatgg aggcatcacc    8100
tggaacttgc tgatggagat tttctatgac cagtacagca acctggatt tgtgaatatc    8160 cttctcccctc ctgatgctaa agagattgcc actcgcttcc gatggtggca gccacgacat    8220
gatggccttg accagaatga ctgggccatt gacaatgtcc tcatctcggg ctctgcggac    8280
cagaggacag tcatgctgga cacctttagc agcgccccag taccacagca tgagcgctcc    8340
cccgcagacg ctggccctgt tggaagaatt gcttttgaaa tgttcttaga agacaaaact    8400
tcagtgaatg agaattggct cttccatgat gactgtacag tggaaagatt ctgtgactcg    8460
ccagatggtg tcatgctctg tggcagccat gatggacgag aggtgtatgc agtgactcat    8520
gacctgacgc ccactgagaa ctggatcatg cagttcaaga tctctgttgg atgcaaagtg    8580
cctgaaaaaa ttgcccagaa tcaaattcac gtgcagttttt ctactgactt tggcgtgagc    8640
tggagttatt tagtccctca gtgcttaccc gccgacccaa agtgttctgg aagcgtttct    8700
caaccgtctg tgttcttccc aactgaaggg tggaaaagga tcacctaccc gcttcctgaa    8760
agcttaacgg ggaatcctgt aagatttagg ttctaccaaa agtactcaga tgtgcagtgg    8820
gcaattgaca atttctacct tggccctgga tgtttggaca actgtggagg ccacggagac    8880
tgcctaaagg aacagtgtat ctgtgaccca ggctactcag gccaaactg ctacttaact    8940 cacagcctga agactttcct gaaggagcgc tttgacagtg aggagatcaa gcctgactta    9000
tggatgtcct tggaaggcgg aagcacttgt acagagtgcg gggtcctcgc cgagaacact    9060
gcactctatt ttgggggatc cactgtgaga caagctatta ctcaagactt agatctcaga    9120
ggtgcaaaat tcctgcagta ctggggacgt atcggcagtg agaacaacat gacatcttgc    9180
catcggcctg tctgccggaa ggaaggcgtg ctgctggact tctctacgga tggaggaatc    9240
acttggacct tgcttcacga gatggatttc cagaaataca tttctgtgag gcacgactac    9300
atcctcctgc ctgaggggc cctcaccaac acaactcgac ttcgctggtg gcagccttt    9360 gtcatcagca atgggctcgt ggtttccggg gtggagcgtg cgcagtgggc actggacaac    9420
attctgattg gtggagcaga aatcaatcca agccaactgg tggacacttt cgatgacgaa    9480
ggctcctccc atgaagaaaa ctggagtttt taccctaatg cagtaaggac agcaggattc    9540
```

-continued

| | |
|---|---|
| tgtggcaacc catccttcca cctctactgg ccaaataaaa agaaggacaa gacccacaat | 9600 |
| gcactctcct cccgagagct cattatacag ccaggataca tgatgcaatt taaaattgtg | 9660 |
| gtgggttgtg aagccacttc atgtggtgac cttcattccg tgatgctgga gtacaccaag | 9720 |
| gatgcaaggt ccgattcctg gcagctcgtg cagacccagt gcctaccttc ctcttccaat | 9780 |
| agcattggct gctccccgtt ccagttccat gaagccacca tttataatgc tgtcaacagc | 9840 |
| tcaagctgga agaggatcac catccagctc ccagaccacg tctcgtcaag tgccacacag | 9900 |
| ttccgctgga tccagaaggg agaagaaacc gagaagcaaa gctgggccat cgaccacgtg | 9960 |
| tacatcggag aggcttgtcc caagctctgc agcgggcatg gctactgcac cacaggggcc | 10020 |
| gtctgcatct gcgatgaaag cttccaaggt gacgactgct ctgtcttcag tcacgagctt | 10080 |
| cctagttaca ttaaagataa ttttgaatca gcaagagtca ctgaagccaa ctgggaaacc | 10140 |
| atccaggtg gagtgatcgg aagtggctgt gggcagctgg cgccctatgc ccatggagat | 10200 |
| tcgctctact ttaatggttg tcagataagg caagctgcca ccaagccact ggacctcact | 10260 |
| cgagcaagca aaattatgtt tgtcttgcaa attgggagcc cagcccagac agacagttgc | 10320 |
| aacagcgacc tcagcggccc ccacaccgtg gacaaagcag tactgctgca gtacagtgtc | 10380 |
| aacaatggca tcacctggca cgtcatcgct cagcaccagc cgaaggactt cacacaagct | 10440 |
| cagcgggtgt cttacaacgt cccctggaa gctcggatga aggagttct actgcgctgg | 10500 |
| tggcagccac gccacaatgg aacaggtcat gatcaatggg cttggacca tgtggaggtc | 10560 |
| gtcctagtaa gcactcgcaa acaaaattac atgatgaatt tttcacggca catgggctc | 10620 |
| aggcacttct acaacagaag acgaaggtcg cttaggcgat acccatgaag aatccaagtt | 10680 |
| tatttcccctt tccagcgtac aatgtgtccc ttcctggttt tttgaaacac ctctcactgc | 10740 |
| atctgatatc aggaaacaaa gatgaaggac ttggcgaaca gaaagccctt cgagatcttg | 10800 |
| tgtaccccac cttcccacac tgtgagctaa tgatgtgtgg tttctctgca cataagtaaa | 10860 |
| tgtcttcacg tcagtgcgtc cgtggaaatt gtgatctgtt gtaatatcag ttacagtggc | 10920 |
| agtattgaga ataagaaata gtttaacagg aaaaaacgtt taagcacaaa cattttaag | 10980 |
| atcttatgtt ttaagtggca ttttagcaca gtatttaaca ttgttggtca ccgagctatt | 11040 |
| taagtagact gtatttcagc tctgtctctt gtttaatatg aataagttct cgtcgtttgt | 11100 |
| cctttatgta ttcttctcta ccgtataaca cactgaaact gtatctactt gctgtgttgc | 11160 |
| aatattttgc tgctggactt tgacctactt gtattatgca gaaagttaat gcagatacct | 11220 |
| attcaagatg ataactgtaa agacactgct gtctccttaa tatgctcctt aacacgtatg | 11280 |
| ttgatgtagc atcattttgt ggataggaaa aaaaatgttt gaccttcaga tattttctac | 11340 |
| ttaaaaaatt gtggatgaac gccctatctc cctcccacag tgagtcccca ttaccttgtc | 11400 |
| taaaacaatt ttttaatgtg ttctgtggcc gttttactga cagtaactgc catttcgtgt | 11460 |
| ctgtggtaac aaagtgactt gtaaaatggt ggatgtttcc ctcactgtgt tctcttcgtg | 11520 |
| ggttgtttcc ttgtgggtca tagtcatacc ttctgatgag gtggagccaa caccagcaaa | 11580 |
| gtatgatggc cctgtagcct ctgactagtc ctgaaacaga aggctgcact ctaggctgaa | 11640 |
| ccatgctaaa agcccatgct taaataaaaa atg | 11673 |

<210> SEQ ID NO 4
<211> LENGTH: 11580
<212> TYPE: DNA
<213> ORGANISM: Homo sapien -continued

```
<400> SEQUENCE: 4
cacgcgtggg ctcggcgggg gcccgctccc aggcccgctc ccgagcccgt tccgctcccg      60
tccgccttct tctcgccttc tctccgcgtg gctcctccgt cccggcgtct ccaaaactga     120
atgagcgagc ggcgcgtagg gcgscggcgg cggcggcggc ggcggcggcg gcggcatgga     180
gcgcagtggc tgggcccggc agactttcct cctagcgctg ttgctggggg cgacgctgag     240
ggcgcgcgcg gcggctggct attacccccg cttttcgccc ttcttttttcc tgtgcaccca     300
ccacggggag ctggaagggg atggggagca gggcgaggtg ctcatttccc tgcatattgc     360
gggcaacccc acctactacg ttccgggaca agaataccat gtgacaattt caacaagcac     420
cttttttgac ggcttgctgg tgacaggact atacacatct acaagtgttc aggcatcaca     480
gagcattgga ggttccagtg ctttcggatt tgggatcatg tctgaccacc agtttggtaa     540
ccagtttatg tgcagtgtgg tagcctctca cgtgagtcac ctgcccacaa ccaacctcag     600
tttcatctgg attgctccac ctgcgggcac aggctgtgtg aatttcatgg ctacagcaac     660
acaccgggc caggttattt tcaaagatgc tttagcccag cagttgtgtg aacaaggagc     720
tccaacagat gtcactgtgc acccacatct agctgaaata catagtgaca gcattatcct     780
gagagatgac tttgactcct accaccaact gcaattaaat ccaaatatat gggttgaatg     840
taacaactgt gagactggag aacagtgtgg cgcgattatg catggcaatg ccgtcacctt     900
ctgtgaacca tatggcccac gagaactgat taccacaggc cttaatacaa caacagcttc     960
tgtcctccaa ttttccattg ggtcaggttc atgtcgcttt agttattcag accccagcat    1020
catcgtgtta tatgccaaga taactctgc ggactggatt cagctagaga aaattagagc    1080
cccttccaat gtcagcacaa tcatccatat cctctacctt cctgaggacg ccaaggggga    1140
gaatgtccaa tttcagtgga agcaggaaaa tcttcgtgta ggtgaagtgt atgaagcctg    1200
ctgggcctta gataacatct tgatcatcaa ttcagctcac agacaagtcg ttttagaaga    1260
tagtctcgac ccagtggaca caggcaactg gcttttcttc ccaggagcta cagttaagca    1320
tagctgtcag tcagatggga actccatta tttccatgga aatgaaggca gcgagttcaa    1380
ttttgccacc accagggatg tagatctttc cacagaagat attcaagagc aatggtcaga    1440
agaatttgag agccagccta caggatggga tgtcttggga gctgtcattg gtacagaatg    1500
tggaacgata gaatcaggct tatcaatggt cttcctcaaa gatggagaga ggaaattatg    1560
cactccatcc atggacacta ccggttatgg gaacctgagg ttttacttttg tgatgggagg    1620
aatttgtgac cctggaaatt ctcatgaaaa tgacataatc ctgtatgcaa aaattgaagg    1680
aagaaaagag catataacac tggatacct ttcctattcc tcatataagg ttccgtcttt    1740
ggtttctgtg gtcatcaatc ctgaacttca gactcctgct accaaatttt gtctcaggca    1800
aaagaaccat caaggacata ataggaatgt ctgggctgta gactttttcc atgtcttgcc    1860
tgttctccct tctacaatgt ctcacatgat acagttttcc atcaatctgg atgtggaac    1920
gcatcagcct ggtaacagtg tcagcttgga attttctacc aaccatgggc gctcctggtc    1980
cctccttcac actgaatgct tacctgagat ctgtgctgga ccccacctcc cccacagcac    2040
tgtctactcc tctgaaaact acagtgggtg gaaccgaata acaattcccc ttcctaacgc    2100
agcactaacc cggaacacca ggattcgctg gagacaaaca ggaccaatcc ttggaaacat    2160
gtgggcaatt gataatgttt atattggccc gtcatgtctc aaattctgtt ctggcagagg    2220
acagtgcact agacatggtt gcaagtgtga ccctggattt tctggcccag cttgtgagat    2280
ggcatcccag acattcccaa tgtttatttc tgaaagcttt ggcagttcca ggctctcctc    2340
```

```
ttaccataac ttttactcta tccgtggtgc tgaagtcagc tttggttgtg gtgtcttggc     2400
cagtggtaag gccctggttt tcaacaaaga agggcggcgt cagctaatta catctttcct     2460
tgacagctca caatccaggt ttctccagtt cacactgaga ctggggagca aatctgttct     2520
gagcacgtgc agagcccctg atcagcctgg tgaaggagtt ttgctgcatt attcttatga     2580
taatgggata acttggaaac tcctggagca ttattcatat ctcagctatc atgagcccag     2640
aataatctcc gtagaactac caggtgatgc aaagcagttt ggaattcagt tcagatggtg     2700
gcaaccgtat cattcttccc agagagaaga tgtatgggct attgatgaga ttatcatgac     2760
atctgtgctt ttcaacagca ttagtcttga ctttaccaat cttgtggagg tcactcagtc     2820
tctgggattc taccttggaa atgttcagcc atactgtggc cacgactgga ccctttgttt     2880
tacaggagat tctaaacttg cctcaagtat gcgctatgtg aaacacaat caatgcagat      2940 aggagcatcc tatatgattc agttcagttt ggtgatggga tgtggccaga atacaccccc     3000
acacatggac aaccaggtga agctggagta ctcaaccaac cacggcctta cctggcacct     3060
cgtccaagaa gaatgccttc caagtatgcc aagttgtcag gaatttacat cagcaagtat     3120
ttaccatgcc agtgagttta cacagtggag gagagtcata gtgcttcttc cccagaaaac     3180
ttggtccagt gctacccgtt ccgctggag ccagagctat tacacagctc aagacgagtg      3240
ggctttggac agcatttaca ttgggcagca gtgcccaac atgtgcagtg gcatggctc       3300 atgcgatcat ggcatatgca ggtgtgacca ggggtaccaa ggcactgaat gccacccaga     3360
agctgcccct ccgtccacaa ttatgtcaga ttttgagaac cagaatggct gggagtctga     3420
ctggcaagaa gttattgggg gagaaattgt aaaaccagaa caagggtgtg gtgtcatctc     3480
ttctggatca tctctgtact tcagcaaggc tgggaaaaga cagctggtga ttgggaccct     3540
ggatacttct tgggtggact ttgtccagtt ctacatccag ataggcggag agagtgcttc     3600
atgcaacaag cctgacagca gagaggaggg cgtcctcctt cagtacagca acaatggggg     3660
catccagtgg cacctgctag cagagatgta cttttcagac ttcagcaaac ccagatttgt     3720
ctatctggag cttccagctg ctgccaagac cccttgcacc aggttccgct ggtggcagcc     3780
cgtgttctca ggggaggact atgaccagtg ggcagtcgat gacatcatca ttctgtccga     3840
gaagcagaag cagatcatcc cagttatcaa tccaacttta cctcagaact tttatgagaa     3900
gccagctttt gattacccta tgaatcagat gagtgtgtgg ttgatgttgg ctaatgaagg     3960
aatggttaaa aatgaaacct tctgtgctgc cacaccatca gcaatgatat ttggaaaatc     4020
agatggagat cgatttgcag taactcgaga tttgaccctg aaacctggat atgtgctaca     4080
gttcaagcta aacataggtt gtgccaatca attcagcagt actgctccag ttcttcttca     4140
gtactctcat gatgctggta tgtcctggtt tctggtgaaa gaaggctgtt acccggcttc     4200
tgcaggcaaa ggatgcgaag gaaactccag agaactaagt gagcccacca tgtatcacac     4260
aggggacttt gaagaatgga caagaatcac cattgttatt ccaaggtctc ttgcatccag     4320
caagaccaga ttccgatgga tccaggagag cagctcacag aaaaacgtgc ctccatttgg     4380
tttagatgga gtgtacatat ccgagccttg tcccagttac tgcagtggcc atggggactg     4440
catttcagga gtgtgtttct gtgacctggg atatactgct gcacaaggaa cctgtgtgtc     4500
aaatgtcccc aatcacaatg agatgttcga taggtttgag gggaagctca gccctctgtg     4560
gtacaagata acaggtgccc aggttggaac tggctgtgga acacttaacg atggcaaatc     4620
tctctacttc aatggccctg ggaaaaggga agcccggacg gtccctctgg acaccaggaa     4680
tatcagactt gttcaatttt atatacaaat tggaagcaaa acttcaggca ttacctgcat     4740
```

```
caaaccaaga actagaaatg aagggcttat tgttcagtat tcaaatgaca atgggatact    4800
ctggcatttg cttcgagagt tggacttcat gtccttcctg aaccacaga tcatttccat    4860 tgacctgcca caggacgcga agacacctgc aacggcattt cgatggtggc aaccgcaaca    4920
tgggaagcat tcagcccagt gggctttgga tgatgttctt ataggaatga atgacagctc    4980
tcaaactgga tttcaagaca aatttgatgg ctctatagat ttgcaagcca actggtatcg    5040
aatccaagga ggtcaagttg atattgactg tctctctatg gatactgctc tgatattcac    5100
tgaaaacata ggaaaacctc gttatgctga gacctgggat tttcatgtgt cagcatctac    5160 cttttttgcag tttgaaatga gcatgggctg tagcaagccc ttcagcaact cccacagtgt    5220
acagctccag tattctctga acaatggcaa ggactgcat cttgtcaccg aagagtgtgt    5280
tcctccaacc attggctgtc tgcattacac ggaaagttca atttacacct cggaaagatt    5340
ccagaattgg aagcggatca ctgtctacct tccactctcc accatttctc ccaggacccg    5400
gttcagatgg attcaggcca actacactgt ggggctgat tcctgggcga ttgataatgt    5460
tgtactggcc tcagggtgcc cttggatgtg ctcaggacga gggatttgtg atgctggacg    5520
ctgtgtgtgt gaccggggct ttggtggacc ctattgtgtt cctgttgttc ctctgccctc    5580
gattcttaaa gacgatttca atgggaattt acatcctgac ctttggcctg aagtgtatgg    5640
tgcagagagg gggaatctga atggtgaaac catcaaatct ggaacatctc taatttttaa    5700
aggggaagga ctaaggatgc ttatttcaag agatctagat tgtacaaata caatgtatgt    5760 ccagtttttca cttagattta tagcaaaaag tacccccagag agatctcact ctattctgtt    5820
acaattctcc atcagtggag gaatcacttg gcacctgatg gatgaattt actttcctca    5880 aacaacgaat atacttttca tcaatgttcc cttgccatac actgcccaaa ccaatgctac    5940
aagattcaga ctctggcaac cttataataa cggtaagaaa gaagaaatct ggattgttga    6000
tgacttcatt atcgatggaa ataatgtaaa caaccctgtg atgctcttgg atacatttga    6060
ttttgggccc agagaagaca attggttttt ctatcctggt ggtaacatcg gtctttattg    6120
tccatattct tcaaggggg cacctgaaga agattcagct atggtgtttg tttcaaatga    6180
agttggtgag cattccatta ccacccgtga cctaaatgtg aatgagaaca ccatcataca    6240
atttgagatc aacgttggct gttcgactga tagctcatcc gcggatccag tgagactgga    6300 atttttcaagg gacttcgggg cgacctggca ccttctgctg cccctctgct accacagcag    6360
cagccacgtc agctctttat gctccaccga gcaccacccc agcagcacct actacgcagg    6420
aaccatgcag ggctggagga gggaggtcgt gcactttggg aagctgcacc tttgtggatc    6480
tgtccgtttc agatggtacc agggatttta ccctgccggc tctcagccag tgacatgggc    6540
cattgataat gtctacatcg gtccccagtg tgaggagatg tgtaatggac aggggagctg    6600
tatcaatgga accaaatgta tatgtgaccc tggctactca ggtccaacct gtaaataag    6660 caccaaaaat cctgattttc tcaaagatga tttcgaaggt cagctagaat ctgatagatt    6720
cttattaatg agtggtggga aaccatctcg aaagtgtgga atcctttcta gtggaaacaa    6780
cctcttttcc aatgaagatg gcttgcgcat gttgatgaca cgagacctgg atttatcaca    6840
tgctagattt gtgcagttct tcatgagact gggatgtggt aaaggcgttc ctgaccccag    6900
gagtcaaccc gtgctcctac agtattctct caacggtggc ctctcgtgga gtcttcttca    6960
ggagttcctt ttcagcaatt ccagcaatgt gggcaggtac attgccctgg agatacctt    7020 gaaagcccgt tctggttcta ctcgccttcg ctggtggcaa ccgtctgaga atgggcactt    7080
ctacagcccc tgggttatcg atcagattct tattggagga aatatttctg gtaatacggt    7140
```

-continued

```
cttggaagat gatttcacaa cccttgatag taggaaatgg ctgcttcacc caggaggcac      7200
caagatgccc gtgtgtggct ctactggtga tgccctggtc ttcattgaaa aggccagcac      7260
ccgttacgtg gtcagcacag acgttgccgt gaatgaggat tccttcctac agatagactt      7320
cgctgcctcc tgctcagtca cagactcttg ttatgcgatt gaattggaat actcagtaga      7380
tcttggattg tcatggcacc cattggtaag ggactgtctg cctaccaatg tggaatgcag      7440
tcgctatcat ctgcaacgga tcctggtgtc agacactttc aacaagtgga ctagaatcac      7500
tctgcctctc cctccttata ccaggtccca agccactcgt ttccgttggc atcaaccagc      7560
tcctttgac aagcagcaga catgggcaat agataatgtc tatatcgggg atggctgcat       7620
agacatgtgc agtggccatg ggagatgcat ccagggaaac tgcgtctgtg atgaacagtg      7680
gggtggcctg tactgtgatg accccgagac ctctcttcca acccaactca agacaactt       7740
caatcgagct ccatccagtc agaactggct gactgtgaac ggagggaaat tgagtacagt      7800
gtgtggagcc gtggcgtcgg gaatggctct ccatttcagt gggggttgta gtcgattatt      7860
agtcactgtg gatctaaacc tcactaatgc tgagttcatc caattttact tcatgtatgg      7920
gtgcctgatt acaccaaaca accgtaacca aggtgttctc ttggaatatt ctgtcaatgg      7980
aggcattacc tggaacctgc tcatggagat tttctatgac cagtacagta agcccggatt      8040
tgtgaatatc cttctccctc ctgatgctaa agagattgcc actcgcttcc gctggtggca      8100
gccaagacat gacggcctgg atcagaacga ctgggccatt gacaatgtcc tcatctcagg      8160
ctctgctgac caaaggaccg ttatgctgga caccttcagc agcgcccag tacccagca       8220
cgagcgctcc cctgcagatg ccggcccctgt cgggaggatc gcctttgaca tgtttatgga     8280
agacaaaact tcagtgaatg agcactggct attccatgat gattgtacag tagaaagatt     8340
ctgtgactcc cctgatggtg tgatgctctg tggcagtcat gatggacggg aggtgtatgc     8400
agtgacccat gacctgactc ccactgaagg ctggattatg caattcaaga tctcagttgg     8460
atgtaaggtg tctgaaaaaa ttgcccagaa tcaaattcat gtgcagtatt ctactgactt     8520
cggtgtgagt tggaattatc tggtccctca gtgcttgcct gctgacccaa aatgctctgg     8580
aagtgtttct cagccatctg tattctttcc aactaaaggg tggaaaagga tcacctaccc     8640
acttcctgaa agcttagtgg gaaatccggt aaggtttagg ttctatcaga agtactcaga     8700
catgcagtgg gcaatcgata atttctacct gggccctgga tgcttggaca actgcagggg     8760
ccatggagat tgcttaaggg aacagtgcat ctgtgatccg ggatactcag ggccaaactg     8820
ctacttgacc cacactctga agactttcct gaaggaacgc tttgacagtg aagaaatcaa     8880
acctgactta tggatgtcct tagaaggtgg aagtacttgc actgagtgtg gaattcttgc     8940
cgaggacact gcactctatt ttgggggatc cactgtgaga caagcggtta cacaagattt     9000
ggatcttcga ggtgcaaagt tcctgcaata ctgggggcgc atcggtagtg agaacaacat     9060
gacctcttgc catcgtccca tctgccggaa ggaaggcgtg ctgttggact actctaccga     9120
tggaggaatt acctggactt tgctccatga gatggattac cagaaataca tttctgttag     9180
acacgactac atacttcttc ctgaagatgc cctcaccaac acaactcgac ttcgctggtg     9240
gcagcctttt gtgatcagca atggaattgt ggtctctggg gtggagcgtg ctcagtgggc     9300
actggacaac attttgattg gtggagcaga atcaatccc agccaattgg tggacacttt      9360
tgatgatgaa ggcacttccc atgaagaaaa ctggagtttt taccctaatg ctgtaaggac     9420
agcaggattt tgtggcaatc catcctttca cctctattgg ccaaataaaa agaaggacaa     9480
gactcacaat gctctctcct cccgagaact cattatacag ccaggataca tgatgcagtt     9540
```

-continued

```
taaaattgtg gtgggttgtg aagccacttc ttgtggtgac cttcattccg taatgctgga    9600
atacactaag gatgcaagat cggattcctg gcagctcgta cagacccagt gccttccttc    9660
ctcttctaac agcattggct gctccccttt ccagttccat gaagccacca tctacaactc    9720
tgtcaacagc tcaagctgga aaagaatcac catccagctg cctgaccatg tctcctctag    9780
tgcaacacag ttccgctgga tccagaaggg agaagaaact gagaagcaaa gctgggcaat    9840
tgaccacgtg tacattggag aggcttgccc caagctctgc agcgggcacg gatactgcac    9900
gaccggtgcc atctgcatct gcgacgagag cttccaaggt gatgactgct ctgttttcag    9960
tcacgacctt cccagttata ttaaagataa ttttgagtcc gcaagagtca ccgaggcaaa   10020
ctgggagacc attcaaggtg gagtcatagg aagtggctgt gggcagctgg cccctacgc    10080
ccatggagac tcactgtact ttaatggctg tcagatcagg caagcagcta ccaagcctct   10140
ggatctcact cgagcaagca aaatcatgtt tgttttgcaa attgggagca tgtcgcagac   10200
ggacagctgc aacagtgacc tgagtggccc ccacgctgtg acaaggcgg tgctgctgca    10260
atacagcgtc aacaacggga tcacctggca tgtcatcgcc cagcaccagc caaaggactt   10320
cacacaagct cagagagtgt cttacaatgt cccctggag gcacggatga aggagtctt     10380
actgcgctgg tggcaaccac gccacaatgg aacaggtcat gatcaatggg ctttggacca   10440
tgtggaggtc gtcctagtaa gcactcgcaa acaaaattac atgatgaatt tttcacgaca   10500
acatggctc agacatttct acaacagaag acgaaggtca cttaggcgat acccatgaag    10560
aatcaaaaag tttattttt tcttccaac atgtgatgtg ttgctctcca ttctttaaa      10620
tctcgcacta catctgatat caggaaatat ctgtgaagga cttggtgatt acctgaaagc   10680
ccttctcaag accgagtgta caccactttc ccacactgtg aactaatgac aagtgactta   10740
tttgctcata agtaaatgtc ttcatgttga tgtgtccgtg aaagttgtga tctgttgtaa   10800
tatcagttac agtggcagta ttgacaataa gaaacagttt aacagaaaaa tgaaatttaa   10860
gcacaaaaaa tttaagagat tttatgttta aaatggcatt tagcacagta tttaacattc   10920
ttggtcacaa agctatttaa gtggactgta tttcagctat gtctcatgtt ttatatgatt   10980
aaattatcat tgtttgtcct ttatgtattc tcttctacaa tacaacacat tgaaactgta   11040
tttacttgtt atgttgtaat attttgctgc tgaatttggg gctacttata ttctgcagaa   11100
aattaattga aatacctatt caagaagata gttgtaaaga tattgtatct cctttaatat   11160
actccttaaa aatgtatgtt ggtttagcgt tgttttgtgg ataagaaaaa tgcttgaccc   11220
tgaaatattt tctactttaa attgtggatg aagaccctat ctcccacaaa taagttccca   11280
tttccttgtc taaagatctt ttttaagtg ttctgtggct gatttactaa cagtaactgc    11340
catttttgt ctgtgataac agagtgattt gtaaaacagt ggttgttttt tcattgtgtt    11400
ttcttcgtgg attgtttttt ctgcgggtca tattcatacc ttctgatgaa gttgtacaac   11460
accagcaaca ttataatggc cctgtagctc tgaatgctat ttgtgtaact gaaaggttgc   11520
actctagggt gaaccaagct ataaaagccc atgcttaaat aaaaattatg tccaaaagcc   11580
```

<210> SEQ ID NO 5
<211> LENGTH: 10
<212> TYPE: PRT
<213> ORGANISM: Homo sapien

<400> SEQUENCE: 5

Gln Lys Leu Ile Ser Glu Glu Asp Leu Asn
 1               5                  10

INTERACTION OF REELIN WITH VERY LOW DENSITY LIPOPROTEIN (VLDL) RECEPTOR FOR SCREENING AND THERAPIES

The work leading to the present invention was supported, in part, by National Institute of Health Grants NS 36558. Thus, the United States Government has certain rights in the invention.

FIELD OF THE INVENTION

The present invention relates to the identification of an interaction between Reelin and the very low density lipoprotein (VLDL) receptor. This allows development of a convenient assay system for receptor binding that is adaptable for screening modulators (agonists and antagonists) of the interaction between Reelin and the VLDL receptor or similar receptors.

BACKGROUND OF THE INVENTION

The complexity of the human brain presents a challenge to scientists striving for an understanding of the molecular basis of neuronal development and function. Nevertheless, advances in genome technologies have led to the identification of several genes, mutated in neurological disorders that are important for brain development and function. Furthermore, the ability to disrupt genes in the mouse germline provides an opportunity to develop models and to test the contributions of specific genes to neurobiological processes. The information obtained from these studies is relevant to human diseases because cellular and molecular mechanisms are largely conserved between mice and humans.

Reelin

Neurological abnormalities affecting behavior or locomotion have been identified frequently in inbred mouse strains. One mutant mouse that has been extensively studied because of its remarkable neurological phenotype is the reeler mouse (reviewed in D'Arcangelo and Curran, Reeler: New Tales on an Old Mutant Mouse, BioEssays, In press, 1998; de Rouvroit and Goffinet, Adv. Anat. Embryol. Cell Biol., 150:1–108, 1998). Reeler is an autosomal recessive mutation in which homozygous mutant mice exhibit ataxia, tremors, imbalance and a typical reeling gait that becomes apparent two weeks after birth. These behavioral defects are associated with severe hypoplasia of the cerebellum which lacks foliation. In addition, reeler mice exhibit neuronal ectopia in laminated brain structures including the cerebral and cerebellar cortices, and the hippocampus. Neurons in brain stem nuclei are also abnormally positioned. This anatomical phenotype indicates that the reeler gene controls cell positioning at the end of the migratory phase of brain development. Correct neuronal positioning is essential for the establishment of appropriate synaptic connectivity and proper brain function. This is emphasized by the findings that in reeler brain the axonal branching, and the synaptic density of cerebellar and hippocampal neurons are aberrant (Del Rio et al., Nature, 385:70–74, 1997; Borrell et al., J. Neurosci., 19:1345–1358, 1999). This abnormal connectivity results in altered expression of genes such as the NMDA receptor subunit genes (Wanatabe et al, Neurosci. Res., 26:335–343, 1996).

A mutant mouse carrying a novel allele of reeler was isolated by insertional mutagenesis (Miao et al., Proc. Natl. Acad. Sci. USA, 91:11050–11054, 1994). This provided a molecular marker that allowed cloning of the reeler gene, which was named reelin (Reln). Reelin is expressed during normal brain development (D'Arcangelo et al., Nature, 374:719–723, 1995); reelin mRNA is very large (approximately 12 kb), and it contains an open reading frame of 10,383 bp. The reelin gene is composed of 65 exons spread over a region of approximately 450 kb (Royaux et al., Genomic Organization of the Mouse Reelin Gene, Genomics, In press, 1997). Using the mouse cDNA as a probe, the human reelin gene was also cloned and sequenced (DeSilva et al., Genome Res., 7:157–164, 1997). The predicted protein encoded by the human gene is 94% identical to the mouse gene indicating an extremely high degree of sequence conservation. This implies that the mouse and human genes are functionally very similar.

During development, reelin is expressed at high levels in the central nervous system, liver and kidney (Ikeda and Terashima, Dev. Dyn., 210:157–172. 1997). In the developing central nervous system, sites of high expression are the cerebral cortex, hippocampus, cerebellum, olfactory bulb, spinal cord and retina (D'Arcangelo et al., supra, 1995; Ogawa et al., Neuron, 14:899–912, 1995; Schiffmann et al., Eur. J. Neurosci., 9:1055–1071, 1997; Alcantara et al., 1998). In the embryonic mouse brain, reelin is expressed mainly by Cajal-Retzius cells in the marginal zone of the developing neocortex and hippocampus, and by granule neurons in the external germinal layer of the cerebellum (D'Arcangelo et al., supra, 1995; Ogawa et al., supra, 1995; Miyata et al., J. Comp. Neurol., 372:215–228, 1996). Similarly, reelin is expressed in the marginal zone of the prenatal human neocortex (Meyer and Goffinet, J. Comp. Neurol., 197:29–40, 1998). In adult mice, reelin is expressed predominantly in the brain, but also in the spinal cord, spleen, thymus, liver, kidney, and gonads (D'Arcangelo et al., supra, 1995; Ikeda and Terashima, supra, 1997). Several populations of cells, distinct from those that express reelin in the embryonic cortex, maintain a high level of reelin expression throughout adult life (Alcantara et al. 1998). Reelin expression is particularly high in the olfactory bulb, in the hippocampus, and in the entorhinal cortex, which projects to the hippocampus. Although the expression of reelin in embryonic brain is clearly linked to the determination of neuronal positioning and the maturation of dendrites and axonal branches during development, the significance of reelin expression in the adult has not yet been clearly established. However, the discovery and characterization of other molecules involved in reelin function suggest that reelin may be important for physiological and pathophysiological processes in the adult brain as well as other organs.

The reelin open reading frame (D'Arcangelo et al., supra, 1995) predicts a novel protein of 3,461 amino acids (approximately 385 kDa). At the N terminus, Reelin contains a cleavable signal peptide and a small region of similarity with F-spondin, a protein secreted by floor plate cells in the developing neural tube. At the C terminus of Reelin there is a stretch of positively charged amino acids. The main body of the protein comprises a series of eight internal repeats of 350–390 amino acids, each containing two related subdomains that flank a pattern of conserved cysteine residues known as an EGF-like motif. These cysteine-rich regions resemble those found in other extracellular proteins, whereas the flanking subdomains appear to be unique to Reelin. Expression studies in transfected mammalian cells and cultured neurons demonstrate that, as predicted by its structural features, Reelin it is indeed an extracellular glycoprotein (D'Arcangelo et al., J. Neurosci., 17:23–31, 1997).

Recently, a signal transduction adaptor molecule, Disabled1 (Dab1) (Howell et al., EMBO J., 16:121–132, 1997a) that plays a key role in the Reelin pathway was identified. This discovery was prompted by the observation that mutant mice lacking Dab1 display a phenotype indistinguishable from that of reeler mice (Howell et al., Nature, 389:733–736, 1997b; Sheldon et al., Nature, 389:730–733, 1997). Dab1 is expressed in the target cells of Reelin, i.e., the neurons that go astray in the mutant mice (Rice et al., Development, 125:3719–3729, 1998). Dab1 is an intracellular molecule that is phosphorylated in the developing brain and in cultured neurons exposed to Reelin (Howell et al., Genes and Dev., 13:643–648, 1999a). These findings point to a critical signaling pathway in which Reelin, secreted by a subset of neurons, acts on other neurons that express Dab1.

The missing link in this emerging pathway is the receptor for Reelin. This receptor is predicted to be a transmembrane protein that detects the presence of Reelin in the extracellular environment and communicates this information to the intracellular environment through interactions with Dab1 (D'Arcangelo and Curran, supra, 1998). Receptor occupancy may lead to phosphorylation of Dab1, and ultimately changes in gene expression in the target cell populations that alter the morphology and properties of neurons necessary for layer formation and neuronal maturation.

Recently, the phenotype of mice lacking the very low density lipoprotein receptor (VLDLR) (Takahashi et al., Proc. Natl. Acad. Sci. USA, 89:9252–9256, 1992) and the apolipoprotein E (ApoE) receptor 2 (ApoER2) (Kim et al., J. Biol. Chem., 271:8373–8380, 1996; Novak et al., J. Biol. Chem., 271:11732–11736, 1996) genes was reported (Trommsdorff et al., J. Biol. Chem., 273:33556–33560, 1999). Remarkably, the anatomical phenotype is identical to that of mice in which the reelin or dab1 genes are disrupted. VLDLR and ApoER2 are members of the low-density lipoprotein receptor (LDLR) family which is important for the regulation of lipid metabolism. The LDLR family comprises five members, LDLR, LDLR-related protein (LRP), Megalin, VLDLR and ApoER2 (reviewed by Krieger and Herz, Annu. Rev. Biochem., 63:601–637, 1994). These are structurally related multifunctional receptors that mediate endocytosis of extracellular ligands. All members of this family can bind ApoE-containing lipoproteins. LDLR also binds ApoB-100 and associated high (HDL), low (LDL) and very low (VLDL) density lipoproteins. The LDLR-related protein (LRP) and Megalin bind, in addition to lipoproteins, a variety of ligands including proteases and their inhibitors, peptide hormones and vitamin carrier proteins. VLDLR and ApoER2 have previously been described as lipoprotein receptors that bind ApoE-containing VLDL. Among family members, VLDLR and ApoER2 are the most closely related genes suggesting that they have overlapping functions. This may explain why the reeler-like phenotype is only apparent in double knock out and not in single knock out mice. VLDLR and ApoER2 are expressed in the developing and postnatal brain in regions that are affected by Reelin (Trommsdorff et al., supra, 1999). These findings raised the possibility that VLDLR and ApoER2 are involved in Reelin signal transduction, perhaps as Reelin receptors.

In another set of revealing studies, Dab1 was shown to bind to the amyloid precursor protein (APP) and the other members of the APP family, the amyloid precursor-like protein 1 (APLP1) and the amyloid precursor like protein 2 (APLP2) (Howell et al., The Disabled-1 PTB Domain Binds to the Internalization Signals of Transmembrane Glycoproteins and to Phospholipids, Mol. Cell Biol., In press, 1999b; Homayouni et al., Dab1 Binds tot eh Cytoplasmic Domain of Amyloid Precursor-like Protein 1, J. Neurosci., In press, 1999). The association of Dab1 with APP-like proteins was mapped to a cytoplasmic region of APP proteins containing the NPxY motif which is involved in clathrin-mediated endocytosis. Furthermore, Dab1 has been shown to bind to LDLR family members including ApoER2, VLDLR, LDLR and LRP, through the same NPxY internalization motif (Trommsdorff et al., Cell, 97:689–701, 1998; Trommsdorff et al., 1999). Binding of Dab1 to APP-family proteins results in increased phosphorylation and co-localization to the intracellular side of the plasma membrane (Homayouni et al., supra, 1999).

Alzheimer Disease

A proteolytic product of APP, APPβ, was first identified as a major constituent of the amyloid plaques that are characteristic of Alzheimer Disease (AD). Furthermore, mutations in APP have been linked to autosomal dominant familial Alzheimer Disease (FAD), the most common form of late-onset dementia (Price and Sisodia, Ann. Rev. Neurosci., 21:479–505, 1998). Thus, there is a great interest in elucidating the role of APP in the pathogenesis of AD. However, surprisingly little is known about the normal function of the APP family. In normal brain, APP can affect differentiation, attachment, survival, and outgrowth of neurons (Small et al., J. Neurosci., 14:2117–2127, 1994; Qiu et al., J. Neurosci., 15:2157–2167, 1995). In addition, different regions of the extracellular domain of APP have been shown to inhibit proteases (Oltersdorf et al., Nature, 341:144–174, 1989; Kitaguchi et al., Nature, 331:530–532, 1988) and to modulate synaptic activity (Morimoto et al., J. Neurosci., 18:9386–9393, 1998; Nalbantoglu et al., Nature, 387:500–505, 1997).

It is interesting that disruption of cyclin dependent kinase 5 (cdk5) and its activating subunit p35 result in neuronal migration defects in cortex similar, though not identical, to those seen in mice lacking Reelin and Dab1 (Oshima et al., 1996; Chae et al., Neuron, 18:29–42, 1997). cdk5 is one of the major protein kinases responsible for hyperphosphorylation of tau protein, a component of the neurofibrillary tangles associated with AD (Imahori and Uchida, J. Biochem., 121:179–188, 1997). In addition, cdk5 immunoreactivity increases in neurons which exhibit early stage neurofibrillary tangles (Pei et al., Brain Res., 797:267–277, 1998). In vitro cdk5 can also phosphorylate Dab1 on serine residues.

Apolipoprotein E

ApoE is the most abundant lipoprotein in the brain and cerebro-spinal fluid (Mahley, Science, 240:622–630, 1988). The finding that apoE expression is dramatically elevated after cortical or nerve lesion have implicated it in the response to injury in the central as well as the peripheral nervous system (Poirier et al., Mol. Brain. Res., 11:97–106, 1991; Skene and Shooter, Proc. Natl. Acad. Sci. USA, 80:4169–4173, 1983). ApoE can bind four-helix bundle growth factors such as ciliary neurotrophic factor (CNTF), and it promotes survival of hippocampal neurons (Gutman et al., J. Neurosci., 17:6114–6121, 1997). Epidemiological studies have shown that ApoE is a susceptibility gene for Alzheimer's Disease (reviewed by Strittmatter and Roses, Proc. Natl. Acad. Sci. USA, 92:4725–4727, 1995). Three major isoforms of apoe, apoE2, apoE3 and apoE4 are encoded by different alleles of the APOE gene locus. The APOE4 allele is correlated with increased risk of early-onset Alzheimer's Disease whereas the APOE2 and APOE3 alleles may be protective (Corder et al., Cell Mol. Life Sci., 54:928–934,1998).

Despite the rapid advancement of knowledge of the role of LDL receptor superfamilies in neuronal development and function, there is still a great amount of information about these processes that remains unknown. Thus, there is a need in the art for identification of elements of the Reelin signal transduction pathway, and in particular identification of the Reelin receptor.

There is a further need in the art for identification of elements of the pathway that are involved in signal transduction mediated by binding of Reelin to its receptor.

These and other needs in the art are addressed by the present invention.

SUMMARY OF THE INVENTION

The present invention provides the discovery that the Reelin receptor is the very low density lipoprotein receptor, which is a member of the low density lipoprotein receptor family. Thus, in one aspect, the invention provides a composition comprising an isolated Reelin polypeptide and an isolated low density lipoprotein receptor (LDLR). Preferably, the LDLR is a very low density lipoprotein receptor (VLDLR). In a specific embodiment, the Reelin polypeptide is detectably labeled. This composition can be employed in a screen for compounds that modulate Reelin binding to an LDLR. Such a screen preferably comprises an automated, automated robotic microprocessor controlled system for adding and removing reagents.

The invention further provides a method of screening for Reelin binding to a Dab1 binding receptor, which method comprises detecting binding of a Reelin polypeptide with a Dab1 binding receptor when they are contacted under conditions that permit binding to occur.

Also provided is a method of screening for a modulator of Reelin activity. The method comprises detecting a change in binding activity of a Reelin polypeptide with VLDLR in the presence of a candidate compound under conditions that permit binding of the Reelin polypeptide to VLDLR, wherein detection of a change in binding activity indicates that the candidate compound is a modulator of Reelin binding activity.

These and other aspects of the invention are described in greater detail in the Detailed Description and Examples, infra.

DETAILED DESCRIPTION OF THE INVENTION

Figure 1:
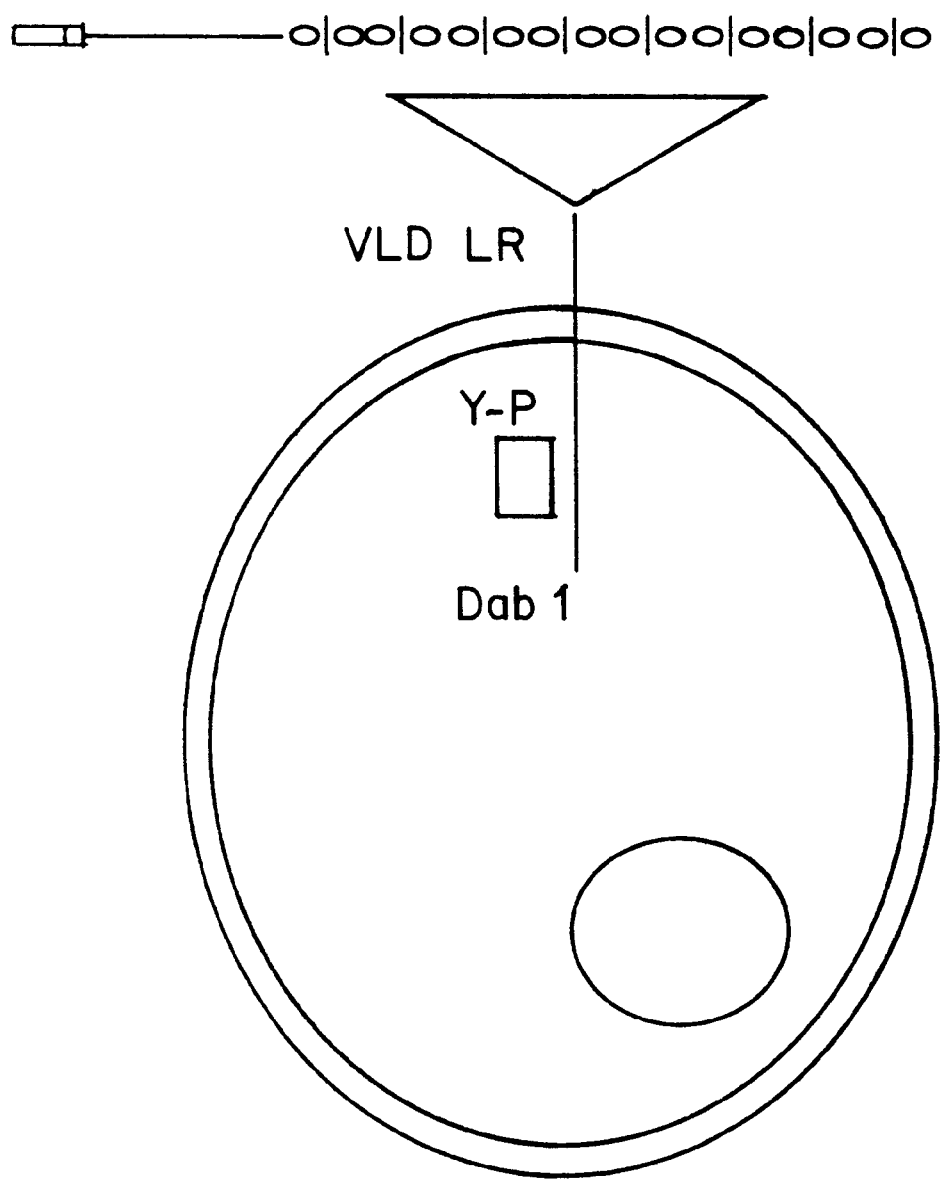
FIG. 1. Schematic drawing of the Reelin/VLDLR interaction. Reelin binds to the VLDLR, which contains a Dab1-clathrin "Y-P" domain. Dab1 binds the receptor in this region.

The present invention is based, in part, on the discovery that Reelin binds to the VLDL receptor, a molecule previously known to bind both ApoF and Dab1. This suggests that the VLDL receptor conveys a signal from Reelin to intracellular molecules in the responsive cell populations. In addition, Dab1 binds to APP family members. Taken together, these results indicate that Reelin, through its interaction with the VLDL receptor, plays an important role both in brain development as well as in the pathogenesis of neurodegenerative diseases, particularly Alzheimer's Disease.

The invention further provides a binding assay for the interaction between Reelin and the VLDL receptor that can be used to identify agents that promote or block this association. Such compounds could be used as therapeutic agents to prevent or alleviate a diverse spectrum of diseases including neurodegenerative disorders such as Alzheimer's Disease, to facilitate neuronal regeneration after injury, to prevent or alleviate lipid metabolism diseases, to enhance cognitive functions and memory, or to ameliorate other developmental disorders.

Although the various components involved in the present invention, such as Reelin and VLDLR, are well known, their ability to directly interact was not known. Thus, in one aspect, the invention provides novel compositions comprising an isolated Reelin polypeptide and an isolated low density lipoprotein receptor, e.g., for testing binding of Reelin to the LDLR or for screening. Such compositions preferably are prepared in an isotonic, buffered aqueous solution.

Definitions

As used herein, a "Reelin polypeptide" means Reelin (the full length protein), a Reelin fusion protein, or a fragment of the Reelin protein that can be tested for binding activity with VLDLR. Reelin polypeptides are described in greater detail below.

As used herein, a "low density lipoprotein receptor (LDLR)" refers to LDLR family members that are characterized by (i) structural similarity; (ii) endocytosis of extracellular ligands; and (iii) binding Apolipoprotein E (ApoE). Preferably an LDLR binds Reelin. Such receptors may interact with Dab1 as well. In a specific, preferred embodiment, the LDLR is very low density lipoprotein receptor (VLDLR) (Oka et al., Genomics 20:298, 1994; human accession no. L22431; mouse accession no. L33417; rat accession no. L35767). Other examples of members of this group presently include ApoER2, low density lipoprotein receptor (LDLR), Megalin, and LDLR-related protein (LRP).

A "Dab1 binding receptor" refers to a receptor that interacts with Dab1. Such receptors are characterized by a NPxY motif in the cytoplasmic domain. Binding of Dab1 to these receptors results in phosphorylation of Dab1. Examples of Dab1 binding receptors include VLDLR, LPR, ApoER2, and the APP family, which includes amyloid precursor protein (APP), amyloid precursor-like protein 1 (APLP1), and APLP2.

A receptor "peptide" is a portion of the receptor, such as an LDLR or a Dab1 binding receptor, that interacts with Reelin or ApoE, or both. Such a peptide can be prepared recombinantly or synthetically for testing in a screen of the invention. In a specific embodiment, the receptor peptide is a LDLR peptide, and more particularly a VLDLR peptide.

"Detectably labeled" means that a polypeptide or other binding partner of a binding pair (including, for example, a small molecule agonist or antagonist of Reelin discovered in a screen of the invention) comprises a molecular entity that directly provides a signal or that interacts with a secondary molecule that is itself detectably labeled. An example of the former is a reporter protein, such as alkaline phosphatase, luciferase, green fluorescent protein, or horseradish peroxidase. An example of the latter is biotin (which binds avidin or streptavidin), an epitope tag, or a hapten group (each of which bind specific antibodies). Any of the labels described herein can be used to detect binding of the secondary binding molecule. In addition to reporter proteins, other labels for direct signal detection include colloidal gold, colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes ($^{125}I$, $^{32}P$, $^{35}S$, chelated Tc, etc.), or magnetic resonance imaging labels.

The term "signal transduction pathway" as used in this invention refers to the intracellular mechanism by which Reelin induces an alteration of cell function or activity, e.g., neuronal differentiation, function, or survival, or hepatocyte function. A key feature of the signal transduction pathway dissected herein is the association of Dab1 with an LDLR and phosphorylation of Dab1 induced by Reelin.

The term "element of a signal transduction pathway" refers to a signal transduction factor that is activated as a result of Reelin binding to an LDLR, particularly VLDLR. In accordance with the present invention, elements of the Reelin signal transduction pathway include Dab1, Dab1 tyrosine and serine kinases, and possibly Cdk5. A "signal" in such a pathway can refer to activation of an element (or factor) in the pathway. For example, activation of Dab1 is a signal of a Reelin/VLDLR binding-induced signal transduction pathway. Generally, activation of one of these factors involves phosphorylation.

"Reelin-induced signaling" and "Reelin-induced signal transduction" refer to the cascade of cellular signals that result from Reelin binding to a cell that expresses a Reelin receptor, particularly VLDLR.

Cells for use in accordance with the invention express a functional Reelin receptor, e.g., VLDLR. Cells that express VLDLR endogenously include neuronal cells and hepatocytes. Alternatively, as mentioned above, cells can be generated using recombinant technology to express the LDLR, preferably in conjunction with Dab1.

The term "inhibitor" is used herein to refer to a compound that can block signalling in the signal transduction pathway described herein. Such an inhibitor may block the pathway at any point, from blocking binding of Reelin to receptor to blocking function of intracellular signal pathways induced by Reelin binding to its receptor.

The term "agonist" is used herein to refer to a compound that can induce signalling in the Reelin/VLDLR signal transduction pathway described herein. Such an inducer may induce the pathway at any point, from mimicking binding of Reelin to a LDLR family member (or an APP family member) to inducing activation of Dab 1. Preferably an agonist discovered in accordance with the invention is specific for signals of Reelin/VLDLR-induced signalling.

"Screening" refers to a process of testing one or a plurality of compounds (including a library of compounds) for some activity. A "screen" is a test system for screening. Screens can be primary, i.e., an initial selection process, or secondary, e.g., to confirm that a compound selected in a primary screen (such as a binding assay) functions as desired (such as in a signal transduction assay). Screening permits the more rapid elimination of irrelevant or non-functional compounds, and thus selection of more relevant compounds for further testing and development. "High throughput screening" involves the automation and robotization of screening systems to rapidly screen a large number of compounds for a desired activity.

As used herein, the term "isolated" means that the referenced material is removed from the environment in which it is normally found. Thus, an isolated biological material can be free of cellular components, i.e., components of the cells in which the material is found or produced in nature. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. As used herein, a membrane protein expressed in a heterologous host cell (i.e., a host cell genetically engineered to express the membrane protein), such as a LDLR, is regarded as "isolated." An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, particularly in biology, the term "about" can mean within an order of magnitude of a given value, and preferably within one-half an order of magnitude of the value.

Thus, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleolide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B.ÊPerbal, *A Prcactical Guide To Molecular Cloning* (1984); F. M. Ausubel et al. (eds.), *Current Protocols in Molecular Biology,* John Wiley & Sons, Inc. (1994).

Molecular Biology—Definitions

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"). A "recombinant DNA molecule" is a DNA molecule that has undergone a molecular biological manipulation.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

In vitro or in vivo expression of Reelin or VLDLR (or any other Reelin receptor characterized herein) may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, 1981, Nature 290:304–310), the promoter contained in the 3 long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296:39–42, 1982); prokaryotic expression vectors such as the β-lactamase promoter (Villa-Kamaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., Cell 38:639–646, 1984; Ornitz et al., Cold Spring Harbor Symp. Quant. Biol. 50:399–409, 1986; MacDonald, Hepatology 7:425–515, 1987); insulin gene control region which is active in pancreatic beta cells (Hanahan, Nature 315:115–122, 1985), albumin gene control region which is active in liver (Pinkert et al., Genes and Devel. 1:268–276, 1987), alpha-fetoprotein gene control region which is active in liver (Krumlauf et al., Mol. Cell. Biol. 5:1639–1648, 1985: Hammer et al., Science 235:53–58, 1987), alpha 1-antitrypsin gene control region which is active in the liver (Kelsey et al., Genes and Devel. 1:161–171, 1987).

A coding sequence is "under the control" or "operatively associated with" of transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g. for the expression of a protein coded for by foreign DNA carried by the vector and introduced to the host cell. Expression systems may include mammalian host cells and vectors. Suitable cells include PC12 cells, COS cells, CHO cells, Hela cells, 293 and 293T (human kidney cells), mouse primary myoblasts, and NIH 3T3 cells. Alternatively, an insect expression system, e.g., using a baculovirus vector, can be employed. The present invention also contemplates yeast and bacterial expression systems.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, a gene is heterologous to the vector DNA in which it is inserted for cloning or expression, and it is heterologous to a host cell containing such a vector, in which it is expressed, e.g., a CHO cell.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position. Sequence conservative variants encoding any of the proteins described herein may be useful in various expression systems, e.g., to incorporate preferred codons in the coding sequence so as to increase expression efficiency, or to incorporate a restriction site to facilitate manipulation of the coding sequence without altering the amino acid sequence.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared. Finally, for purposes of the invention, a functional-conservative variant includes a truncated or form of the protein that performs its function, such as truncated Reelin protein, ApeE1 peptide, or LDLR peptide.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA), and Clustal W analysis (MacVector). Sequence comparison algorithms can also be found at at a bioinformatics website (bioinformatics.html)@nwfsc.noaa.gov on the Worldwide Web (www).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of a Reelin polypeptide or an LDLR or APP protein or peptide. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of one or more specific proteins, e.g., to block ApoER2 expression while permitting VLDLR expression. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. Nos. 5,814,500; 5,811,234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br, CN; $CF_3$; $OCF_3$; O-; S-, or N-alkyl; O-, S-, or N-alkenyl; $SOCH_3$; $SO_2CH_3$; $ONO_2$;$NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group.

Nucleotide units having nucleosides other than adenosine, cytidine, guanosine, thymidine and uridine, such as inosine, may be used in an oligonucleotide molecule.

Vectors

A wide variety of host/expression vector combinations may be employed in expressing DNA sequences encoding Reelin, Reelin receptor, and any intracellular signal transduction factors. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., Gene 67:31–40, 1988), pMB9 and their derivatives, plasmids such as RP4; phage DNAS, e.g, the numerous derivatives of phage 1, e.g., NM989, and other phage DNA, e.g., M13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

A vector can be introduced in vivo in a non-viral vector, e.g., by lipofection, with other transfection facilitating agents (peptides, polymers, etc.), or as naked DNA. Synthetic cationic lipids can be used to prepare liposomes for in vivo transfection, with targeting in some instances (Felgner, et. al., Proc. Natl. Acad. Sci. U.S.A. 84:7413–7417, 1987; Felgner and Ringold, Science 337:387–388, 1989; see Mackey, et al., Proc. Natl. Acad. Sci. U.S.A. 85:8027–8031, 1988; Ulmer et al., Science 259:1745–1748, 1993). Useful lipid compounds and compositions for transfer of nucleic acids are described in International Patent Publications WO95/18863 and WO96/17823, and in U.S. Pat. No. 5,459, 127. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931). Recently, a relatively low voltage, high efficiency in vivo DNA transfer technique, termed electrotransfer, has been described (Mir et al., C. P. Acad. Sci., 321:893, 1998; WO 99/01157; WO 99/01158; WO 99/01175). DNA vectors for gene therapy can be introduced into the desired host cells by methods known in the art, e.g., electroporation, microinjection, cell fusion, DEAE dextran, calcium phosphate precipitation, use of a gene gun (ballistic transfection), or use of a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal.

Also useful are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional protein or polypeptide (as set forth above) can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320–330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 90:626–630. 1992; see also La Salle et al., Science 259:988–990, 1993); and a defective adeno-associated virus vector (Samulski et al., J. Virol. 61:3096–3101, 1987; Samulski et al., J. Virol. 63:3822–3828, 1989; Lebkowski et al., Mol. Cell. Biol. 8:3988–3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden. Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, e.g., to create an transient transgenic animal, an appropriate immunosuppressive treatment is employed in conjunction with the viral vector, e.g., adenovirus vector, to avoid immunodeactivation of the viral vector and transfected cells. For example, immunosuppressive cytokines, such as interleukin-10 (IL-10), interleukin-12 (IL-12), interferon-γ (IFN-γ), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Synthetic Peptides

The term "peptide" is used in its broadest sense to refer to a compound of two or more subunit amino acids, amino acid analogs or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D or L optical isomers, and amino acid analogs and peptidomimetics. Thus, peptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties to peptides in the library. Additionally, by assigning specific amino acids at specific coupling steps, peptide libraries with α-helices, β turns, β sheets, γ-turns, and cyclic peptides can be generated. A peptide of three or more amino acids is commonly called an oligopeptide if the peptide chain is short. If the peptide chain is long, the peptide is commonly called a polypeptide or a protein.

The coupling of the amino acids may be accomplished by techniques familiar to those in the art and provided, for example, in Stewart and Young, 1984, Solid Phase Synthesis, Second Edition, Pierce Chemical Co., Rockford, Ill. Amino acids used for peptide synthesis may be standard Boc (Nα-amino protected Nα-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile Nα-amino protected 9-fluorenylmethoxycarbonyl (Fmoc) amino acids first described by Carpino and Han (1972, J. Org. Chem. 37:3403–3409). Both Fmoc and Boc α-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other Nα-protecting groups that are familiar to those skilled in this art. Many methods of activation may be used in the practice of the invention and include, for example, preformed symmetrical anhydrides (PSA), preformed mixed anhydride (PMA), acid chlorides, active esters, and in situ activation of the carboxylic acid, as set forth in Fields and Noble, "Solid phase peptide synthesis utilizing 9-fluorenylmethoxycarbonyl amino acids", Int. J. Pept. Protein Res. 35:161–214, 1990. Solid phase peptide synthesis may be accomplished by techniques familiar to those in the art and provided, for example, in Stewart and Young, 1984. Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS.

The completeness of coupling should be assessed. Those skilled in the art would be familiar with the well known quantitative monitoring tests such as ninhydrin (the Kaiser test), picric acid, 2,4,6-trinitro-benzenesulfonic (TNBS), fluorescamine, and chloranil, which are based on reagent reaction with free amino groups to produce a chromophoric compound. If imino acids (e.g., Pro and Hyp) are used, isatin monitoring is a preferred method. Fields and Noble, supra. Quantification of reaction completeness may be monitored during the course of the reaction, e.g., as described by Salisbury et al. (International Patent Publication No. WO91/03485).

If the coupling reaction is incomplete as determined by this test, the reaction can be forced to completion by several methods familiar to those in the art, including (a) a second coupling using a one to five fold excess of protected amino acid, (b) an additional coupling using different or additional solvents (e.g., trifluoroethane), or (c) the addition of chaotropic salts, e.g., $NaClO_4$ or LiBr (Klis and Stewart, 1990, "Peptides: Chemistry, Structure and Biology," Rivier and Marshall, eds., ESCOM Publ., p. 904–906).

The following non-classical amino acids may be incorporated in peptyides of the invention to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3 R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); b-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); μ-helix inducing analogs (Kemp et al., 1988. Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436.

Reelin Polypeptides

As noted above, the term Reelin polypeptides includes full length Reelin, Reelin fusion proteins, and Reelin fragments.

Full length Reelin. Murine reelin cDNA and genomic clones have been obtained (D'Arcangelo et al., supra, 1995; Royaux et al., supra, 1997). The human reelin gene has also been cloned and sequenced (DeSilva et al., supra, 1997). The predicted protein encoded by the human gene (SEQ ID NO:1) is 94% identical to the mouse gene product (SEQ ID NO:2) indicating an extremely high degree of sequence conservation. This implies that the mouse and human genes are functionally very similar.

The reelin open reading frame predicts a novel protein of 3,461 amino acids (approximately 385 kDa). At the N terminus, Reelin contains a cleavable signal peptide and a small region of similarity with F-spondin, a protein secreted by floor plate cells in the developing neural tube. At the C terminus of Reelin there is a stretch of positively charged amino acids. The main body of the protein comprises a series of eight internal repeats of 350–390 amino acids, each containing two related subdomains that flank a pattern of conserved cysteine residues known as an EGF-like motif. These cysteine-rich regions resemble those found in other extracellular proteins, whereas the flanking subdomains appear to be unique to Reelin. Expression studies in transfected mammalian cells and cultured neurons demonstrate that, as predicted by its structural features, Reelin it is indeed an extracellular glycoprotein (D'Arcangelo et al., supra, 1997).

In adult mice, reelin is expressed predominantly in the brain, but also in the spinal cord, spleen, thymus, liver, kidney, and gonads (D'Arcangelo et al, supra, 1995; Ikeda and Terashima, supra, 1997). Several populations of cells, distinct from those that express reelin in the embryonic cortex, maintain a high level of reelin expression throughout adult life. Reelin expression is particularly high in the olfactory bulb, in the hippocampus, and in the entorhinal cortex, which projects to the hippocampus.

Reelin fusion proteins. Various chimeric constructs prepared by fusing a Reelin amino acid sequence with a non-Reelin amino acid sequence (or "heterologous" sequence) are contemplated as well. Preferably, the heterologous sequence provides some functional activity. In a specific embodiment, the heterologous sequences acts as a detectable label. However, the presence of the heterologous sequence does not adversely impact Reelin's binding to VLDLR.

For example, Reelin can be tagged with an N-terminal or C-terminal tag, such as Myc, FLAG, glutathione-S-transferase (GST), or another such tag for detectable antibody binding or immuno-precipitation. Use of a Myc tag, which is recognized by a commercially available monoclonal antibody (9E10; Babco), is described in an Example, infra.

Reelin can also be fused with a reporter protein, such as alkaline phosphatase, horseradish peroxidase, β-lactamase, β-galactosidase, luciferase, green fluorescent protein, and the like. In a specific embodiment, exemplified infra, Reelin is fused to alkaline phosphatase.

Alternatively, a signal sequence can be substituted for the endogenous signal sequence for more efficient processing into the rough endoplasmic reticulum, golgi, and cell membrane. Similarly, an expression tag, such as an α-mating factor sequence for yeast expression, or residual amino acid residues from a recombinant construct, may be present.

In yet another embodiment, a chromatographic tag or handle can be joined to Reelin. For example, a polyhistidine sequence permits purification on a nickel chelation column.

Reelin protein fragments and deletion muitants. Preliminary analysis has indicated that truncated Reelin peptides are capable of binding to the VLDL receptor. Various Reelin peptides and deletion constructs can be prepared for testing in the screen of the invention. Such testing can be used, for example, to delimit the smallest region of Reelin capable of binding to the VLDL receptor. This can be carried out by a combination of deletion mutagenesis analysis and peptide synthesis (as described above). These peptides may act as agonists for the receptor or they may block binding of full-length Reelin to the VLDL receptor without activating the signal transduction pathway that phosphorylates Dab1. This allows identification of peptides with unique properties.

Truncated Reelin peptides may be N-terminal, C-terminal, or they may contain internal fragments comprising some of the Reelin repreats. Because some of the natural truncations of Reelin bind to the receptor (250K and 150K Reelin, for example) contain the N-terminal epitopes of CR-50 and G10. the C-terminal region is not essential for VLDLR binding. However, the 150K Reelin protein does not bind as well as the 250K or the full length variants, so some of the C-terminal region may contain part of the essential binding domain.

Receptor and ApoE Peptides

Reelin has been shown to bind to VLDLR. In addition, preliminary results have indicated that ApoE inhibits the binding of Reelin to the VLDL receptor. The techniques described above, including deletion mutagenesis and peptide synthesis, for preparation of Reelin peptides can be used to delimit the region of the VLDL receptor that interacts with Reelin, ApoE, or both; and the region of ApoE that interacts with VLDL, and Reelin, or both. Truncated VLDL receptor peptide may specifically block the action of Reelin. In addition, Reelin and VLDL receptor peptides can be used in competition assays with ApoE. This may allow identification of peptides with unique properties.

VLDLR peptides or fragments that block Reelin function will be found in N-terminal regions of the receptor located in the extracellular domain (these should act as competetive inhibitors of Reelin binding). C-terminal regions of the receptor form the intracellular domain and may interfer with Reelin signaling. For example, a peptide containing the Y-P domain may block Dab1 binding to VLDLR or another Reelin receptor, thus preventing signal transduction.

Screening Assays

As exemplified in the Example, infra, the present invention further provides various screening assays for Reelin/VLDLR-induced activation. The assays of the invention are particularly advantageous by permitting rapid evaluation of cellular response. Biological assays, which depend on cell growth, survival, or some other response require substantial amounts of time and resources to evaluate. By detecting individual signals in the Reelin/VLDLR-induced signal transduction pathway, the present invention short-circuits the more tedious and time consuming biological assays. Furthermore, the signal transduction assays can often be performed with very small amounts of material.

In general, a screening assay of the invention makes use of the cells described above, Reelin, and a candidate compound for testing.

The present invention contemplates screens for small molecule compounds, including ligand analogs and mimics, as well as screens for natural compounds that bind to and agonize or antagonize Reelin signal transduction in vivo. Such agonists or antagonists may, for example, interfere in the phosphorylation or dephosphorylation of signal transduction proteins. For example, natural products libraries can be screened using assays of the invention for such molecules. As used herein, the term "compound" refers to any molecule or complex of more than one molecule that affects Reelin/VLDLR-induced signal transduction. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include proteins and peptide fragments, peptides, nucleic acids and oligonucleotides (particularly triple-helix-forming oligonucleotides), carbohydrates, phospholipids and other lipid derivatives, steroids and steroid derivatives, prostaglandins and related arachadonic acid derivatives, etc. Of particular interest are peptides and peptide mimetics, e.g., corresponding to the binding domains of Reelin, VLDLR, or ApoE for each other.

One approach to identifying such compounds uses recombinant bacteriophage to produce large libraries. Using the "phage method" (Scott and Smith, Science 249:386–390, 1990; Cwirla, et al., Proc. Natl. Acad. Sci., 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology 23:709–715, 1986; Geysen et al. J. Immunologic Method 102:259–274, 1987; and the method of Fodor et al. (Science 251:767–773, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic combinatorial libraries (Needels et al., Proc. Natl. Acad. Sci. USA 90:10700–4, 1993; Ohlmeyer et al., Proc. Natl. Acad. Sci. USA 90:10922–10926, 1993; Lam et al., International Patent Publication No. WO 92/00252; Kocis et al., International Patent Publication No. WO 9428028) and the like can be used to screen for compounds according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means (Blondelle et al., Tib Tech, 14:60, 1996).

Binding Assays

A cell-based assay can be used to screen a few or large numbers of peptides or chemical compounds for their ability to modulate the binding of Reelin to the VLDL receptor. Mammalian or insect cells expressing the human VLDL receptor are produced in large scale using the expression constructs described above. Suitable mammalian cells include, but are not limited to, 293T, Jurkat, Hela, COS, CHO, MEF, or NIH3T3 cells. Insect cells may be SF9 or derivatives of this line. Cells are seeded on microplate dishes, rinsed with phosphate buffered saline (PBS). and overlaid with medium containing Reelin, Reelin-fusion proteins, or Reelin peptides. Cells are then washed with PBS and solubilized in the well by the addition of a detergent-containing buffer such as TxB buffer supplemented with protease inhibitors. We have found that, under similar conditions, the binding of Reelin to the VLDL receptor is highly specific. This method can be modified to use fixed, rather than live cells in the binding assay. Microplate dishes are centrifuged to remove the insoluble material, and the soluble cellular proteins are analyzed to detect the presence of Reelin.

The method of detection will vary depending upon the particular form of Reelin used in the binding assay. When Alkaline Phosphatase-Reelin fusion proteins are employed, detection can be accomplished using a colorimetric system to measure the enzymatic activity of Alkaline Phosphatase. Alternatively, immunodetection can be performed using antibodies against an epitope tag or against Reelin itself. Secondary antibodies conjugated to a fluorophor such as FITC or Texas Red, or antibodies conjugated to an enzyme such as Alkaline Phosphatase or Horse Radish Peroxidase can be employed. The staining is then analyzed using a fluorimeter or a spectrophotometer. Additionally, Reelin can be radiolabeled, for example by iodination with $^{125}$I or $^{32}$P to allow detection by autoradiography or scintillation detection, or Reelin could be biotinylated to allow detection by streptavidin-linked reagents.

In addition to cell-based assay systems, cell-free binding assays can be used to screen for agonists and antagonists of the interactions among Reelin, the VLDL receptor and ApoE. Purified proteins or cell extracts can be used in which one of the partners is immobilized on beads or in microtiter wells and the other is used in soluble form. The same approaches to detection of the interaction using fusion proteins, enzyme-linked assays, antibodies and radioisotopes as described above. Alternatively, a BioCore binding assay system can be employed to identify binding interactions in a cell-free system. This will allow the rapid analysis of compounds or natural products in a high throughput screen that does not require cell culture.

The binding assays of the invention can be adapted for high-throughput screens, e.g., using automated systems. Preferably such systems are microprocessor controlled. These systems automatically add and remove reagents from a large number of individual reactions, usually in a microwell array, and are often adapted to read results as well (e.g., by detecting fluorescence or some other output signal). Both cell and cell-free binding assays can be adapted to the high-throughput format.

The Reelin, receptor (e.g., VLDLR), and ApoE peptides described above can be produced for testing in binding assays to determine interesting properties of such peptides. These properties may include:
1) Reelin peptides that activate the VLDL receptor
2) Reelin peptides that block activation of the VLDL receptor by Reelin but not ApoE
3) Reelin peptides that block activation of the VLDL receptor by ApoE but not Reelin
4) Reelin peptides that block activation of the VLDL receptor by ApoE and by Reelin
5) VLDL receptor peptides that block activation of the VLDL receptor by Reelin but not ApoE
6) VLDL receptor peptides that block activation of the VLDL receptor by ApoE but not Reelin
7) VLDL receptor peptides that block activation of the VLDL receptor by ApoE and Reelin The binding assay may also be used to investigate the effect of ApoE peptides on the interaction between Reelin and the VLDL receptor. The region of ApoE responsible for this effect may be delimited by deletion analysis and the synthesis of ApoE peptides. After defining the minimum peptide region necessary for the interactions among Reelin, the VLDL receptor and ApoE, mutagenesis studies can identify peptides that exhibit higher binding affinities. The properties of the available ApoE isoforms (ApoE2, ApoE3 and ApoE4) can be determined in each of the assays.

The analysis described above will allow the identification of amino acid sequences that are critical for the binding of Reelin and ApoE to the VLDL receptor. Based on this information, it is possible to determine the structural features of these binding regions, separately and as complexes, using techniques such as X-ray crystallography, neutron diffraction, nuclear magnetic resonance spectrometry together with bioinformatic approaches. The knowledge of the structure of each of the binding interfaces involved in the transmission of the Reelin and ApoE signals through the VLDL receptor will facilitate the rational design or identification of agonists and antagonists of Reelin or ApoE. In particular, synthetic peptides or peptidomimetics, as described above, can be prepared based on this information.

In addition to the binding assays described above to probe the regions of Reelin, VLDLR, and ApoE that interact with each other, binding assays of the invention will permit evaluation of Reelin binding to any member of the LDLR family. There are several members of the LDL receptor family that share significant sequence similarity (e.g., LDL receptor, Megalin, LRP, and ApoER2). In addition, the APP family proteins interact with Dab1, which appears to be the signal transduction molecule involved in Reelin/VLDLR-induced signalling. All of these receptors can be used in the assays described above to investigate the specificity of the protein-protein and compound-protein interactions described. This may allow identification of compounds that would specifically inhibit or promote Reelin binding, or ApoE binding to individual receptors.

Methods for Detecting Signals

The present invention provides numerous methods for detecting signals, including but not limited to directly detecting phosphorylation of proteins using radioactive phosphorous compounds, indirectly detecting phosphorylation with antibodies specific for phosphorylated epitopes, or detecting signals from activated signal transduction proteins, such as gene expression. Preferably, gene expression is detected using a reporter gene assay. Alternatively, a downstream element of a signal transduction pathway can be modified to have reporter activity. Reporter genes for use in the invention encode detectable proteins, including, but are by no means limited to, chloramphenicol transferase (CAT), β-galactosidase (β-gal), luciferase, green fluorescent protein, alkaline phosphatase, and other genes that can be detected, e.g., immunologically (by antibody assay).

The best characterized intracellular signaling molecule activated in response to the binding of Reelin to its receptor is Dab1. Dab1 is phosphorylated on tyrosine in response to Reelin (Howell et al., 1999a). Binding of Reelin to its receptor may induce the formation of a cytoplasmic tertiary or quaternary complex including the receptor (e.g., VLDLR), Dab1, and a Dab1 kinase or kinases. The assay of the invention can be used to identify molecules that interfere with Reelin/VLDLR-induced signal transduction at the Dab1 level, i.e., that do not affect Reelin binding to VLDLR. In particular, identification of the site of Dab1 phosphorylation may permit its use as a potential target for agonists and antagonists.

Cdk5 phosphorylates Dab1 in vitro. We can screen for inhibitors and agonists of this activity in connection with Reelin binding to VLDLR, and map the phosphorylation sites. Cdk5 has been implicated as a kinase associated with increased phosphorylation of neurofibrillary tangles in AD. Thus, this area of exploration has significant relevance.

Dab1 interacts with APP and LDL receptor families. This involves the Protein Interaction Domain of Dab1 and the NPxY motif of APP and LDL, receptor family members. Assays can be developed as described above to identify agonists and antagonists of these interactions which are critical for the function of Reelin, Dab1 and the VLDL receptor.

Modulation of Reelin Activity

The present invention provides for modulating the activity of Reelin, Apolipoproteins, and LDL receptor family members. For example, the uptake of a variety of extracellular ligands including Reelin and ApoE may be beneficial to neurons or other cell types. This may result in improved neuronal survival or function in neurodegenerative disorders such as AD. Similarly, uptake of Reelin and ApoE through VLDL receptor or other LDL receptor family members could protect neurons from the damage resulting from many types of injury. For example, it could prevent cell death due to ischemia resulting from a stroke in the brain, or it could aid regeneration of lesioned nerves in the spinal cord. The high expression of Reelin in regions of the brain involved in learning and memory also suggests that drugs that modulate the Reelin signaling pathway through the VLDL receptor may produce cognitive enhancement and be beneficial in curing aging associated dementia. Furthermore, because Reelin is present in the liver throughout life, it is possible that drugs affecting Reelin and the VLDL receptor can be used in therapy of lipid and cholesterol metabolism diseases, including atherosclerosis. Other possible utilities of the present invention include the use of drugs identified or designed based on the Reelin-VLDL receptor binding properties in the medical intervention of developmental disorders. These disorders may include neuronal migration defects, including those that result in cortical displasia and epilepsy.

In Vivo Testing Using Transgenic Animals

Transgenic mammals can be prepared for evaluating the molecular mechanisms of Reelin, and particularly human Reelin/VLDLR-induced signaling. Such mammals provide excellent models for screening or testing drug candidates. Thus, human Reelin or VLDLR, or both (double transgenics), "knock-in" mammals can be prepared for evaluating the molecular biology of this system in greater detail than is possible with human subjects. It is also possible to evaluate compounds or diseases on "knockout" animals, e.g., to identify a compound that can compensate for a defect in Reelin acitivity. Both technologies permit manipulation of single units of genetic information in their natural position in a cell genome and to examine the results of that manipulation in the background of a terminally differentiated organism.

A "knock-in" mammal is a mammal in which an endogenous gene is substituted with a heterologous gene (Roemer et al., New Biol. 3:331, 1991). Preferably, the heterologous gene is "knocked-in" to a locus of interest, either the subject of evaluation(in which case the gene may be a reporter gene; see Elefanty et al., Proc Natl Acad Sci USA 95:11897,1998) of expression or function of a homologous gene, thereby linking the heterologous gene expression to transcription from the appropriate promoter. This can be achieved by homologous recombination, transposon (Westphal and Leder, Curr Biol 7:530, 1997), using mutant recombination sites (Araki et al., Nucleic Acids Res 25:868, 1997) or PCR (Zhang and Henderson, Biotechniques 25:784, 1998).

A "knockout mammal" is a mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild-type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 9:2623–34, 1995) describes PPCA knock-out mice.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

Generally, for homologous recombination, the DNA will be at least about 1 kilobase (kb) in length and preferably 3–4 kb in length, thereby providing sufficient complementary sequence for recombination when the knockout construct is introduced into the genomic DNA of the ES cell (discussed below).

Included within the scope of this invention is a mammal in which two or more genes have been knocked out or knocked in, or both. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. Nos. 4,959,317 and 5,801,030).

In another series of embodiments, transgenic animals are created in which (i) a human Reelin or VLDLR, or both, is stably inserted into the genome of the transgenic animal; and/or (ii) the endogenous Reelin or VLDLR, or both, genes are inactivated and replaced with their human counterparts. See, e.g., Coffman, Semin. Nephrol. 17:404, 1997; Esther et al., Lab. Invest. 74:953, 1996; Murakami et al., Blood Press. Suppl. 2:36, 1996. Such animals can be treated with candidate compounds and monitored for neuronal development, neurodegeneration, or efficacy of a candidate therapeutic compound.

Gene Therapy to Modulate Reelin Activity

A gene encoding a truncated or mutant Reelin, VLDLR, or ApoE protein or polypeptide characterized using a screen of the invention can be introduced in vivo, ex vivo, or in vitro using a viral or a non-viral vector, e.g., as discussed above. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-$\gamma$ (IFN-$\gamma$), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Adenovirus vectors. Adenoviruses are eukaryotic DNA viruses that can be modified to efficiently deliver a nucleic acid of the invention to a variety of cell types in vivo, and has been used extensively in gene therapy protocols. Various serotypes of adenovirus exist. Of these serotypes, preference is given to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) orioin. Preferably, the adenovirus of animal origin is a canine adenovirus, more preferably a CAV2 adenovirus (e.g., Manhattan or A26/61 strain (ATCC VR-800), for example). Various replication defective adenovirus and minimum adenovirus vectors have been described for gene therapy (WO94/26914, WO95/02697, WO94/28938, WO94/28152, WO94/12649, WO95/02697

WO96/22378). The replication defective recombinant adenoviruses according to the invention can be prepared by any technique known to the person skilled in the art (Levrero et al., Gene 101:195 1991; EP 185 573; Graham, EMBO J. 3:2917, 1984; Graham et al., J. Gen. Virol. 36:59 1977). Recombinant adenoviruses are recovered and purified using standard molecular biological techniques, which are well known to one of ordinary skill in the art.

Adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see WO 91/18088; WO 93/09239; U.S. Pat. Nos. 4,797,368, 5,139,941, EP 488 528). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as MoMuLV ("murine Moloney leukaemia virus"), MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (WO 90/02806) and the GP+envAM-12 cell line (WO 89/07150). In addition, the recombinant retroviral vectors can contain modifications within the LTRs for suppressing transcriptional activity as well as extensive encapsidation sequences which may include a part of the gag gene (Bender et al., J. Virol. 61:1639, 1987). Recombinant retroviral vectors are purified by standard techniques known to those having ordinary skill in the art.

Retrovirus vectors can also be introduced by recombinant DNA viruses, which permits one cycle of retroviral replication and amplifies transfection efficiency (see WO 95/22617, WO 95/26411, WO 96/39036, WO 97/19182).

Lentivirus vectors. In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest. For a review, see, Naldini, Curr. Opin. Biotechnol., 9:457–63, 1998; see also Zufferey, et al., J. Virol., 72:9873–80, 1998). Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than 106 IU/ml for at least 3 to 4 days (Kafri, et al., J. Virol., 73: 576–584, 1999). The vector produced by the inducible cell line can be concentrated as needed for efficiently transducing nondividing cells in vitro and in vivo.

Non-viral vectors. In another embodiment, the vector can be introduced in vivo using any of the non-viral vector strategies discussed above in connection with "Vectors", e.g., by lipofection, with other transfection facilitating agents (peptides, polymers, etc.), electroporation, electrotransfer, microinjection, cell fusion, DEAE dextran, calcium phosphate precipitation, use of a gene gun, or use of a DNA vector transporter.

EXAMPLES

The present invention will be better understood by reference to the following, examples, which are provided by way of exemplification and are not intended to limit the invention.

Example 1

Development of a Reelin/VLDLR Assay System

This Example describes a cell-based assay to screen large numbers of peptides or chemical compounds for their ability to modulate the binding of Reelin to the VLDL receptor.

Materials and Methods

Construction of reelin clones. The entire reelin open reading frame was assembled by fusing five overlapping cDNA clones isolated from a cerebellum library (D'Arcangelo et al., supra, 1995) and subcloning them into the vector pcDNA3 (Invitrogen) (D'Arcangelo et al., supra, 1997). This vector allows mammalian expression from the human cytomegalovirus (CMV) promoter or in vitro transcription from the T7 promoter. The following reelin fragments were used: 1.2 kb NaeI-SalI from p5'BS1; 1.3 kb SalI-NdeI from pBS2; 3.1 kb NdeI-BspEI from pBS6; 770 bp BspEI-ApaLI from p3Rea3; and 4.2 kb ApaLI-EcoRV from pBS53. The final clone (pCr1) contains the entire reelin open reading frame (10,383 bp), plus 95 bp of sequence 5' to the initiator methionine codon and 82 bp of 3' untranslated sequence (reelin cDNA nucleotides 188–10,748). To produce an epitope-tagged version of Reelin (pCr1M), oligonucleotides encoding the human c-Myc epitope 9E10 (QKLISEEDLN) (SEQ ID NO:5) flanked by BspEI restriction site sequences were annealed and inserted, in frame, into the unique BspEI site present in pCr1. The nucleotide sequence of the mouse reelin cDNA has been deposited in GenBank and the accession number is U24703 (SEQ ID NO:3). We also obtained a human reelin cDNA from a human fetal brain phage library using a fragment of the mouse cDNA as a probe (DeSilva et al., supra, 1997). The composite nucleotide sequence of the human reelin mRNA has been derived and deposited in the GenBank database with the accession number U797 16 (SEQ ID NO:4). This sequence information can be used to isolate cDNA clones by standard procedures and assemble a full-length reelin clone as described for the mouse gene above. This clone can then be inserted into suitable expression plasmid or viral vectors for expression in mammalian, insect, bacterial, and yeast cells.

Reelin production in mammalian cells. To express Reelin, 293T cells are cultured in Dulbecco's Modified Eagle Medium (DMEM, Bio-Whittaker) supplemented with 10% fetal bovine serum (Life Technologies, Inc) in 60 mm tissue culture dishes. On the day following splitting, cells are transfected with pCr1 or pCr1M plasmids using the Fugene6 reagent (Boehringer Mannheim) according to the manufacturer's instructions. One day after transfection the culture medium is replaced with 2 ml of serum-reduced medium (Nephrigen, Celox Inc.) and conditioned for two more days. At that time, the Reelin-enriched medium is collected and stored at 40° C. for up to three weeks without a significant reduction of activity. Routinely, we obtain about 1 $\mu$g/ml Reelin in the conditioned medium. When necessary, Reelin is concentrated by centrifugation using Centricon 100 filters (Ambion Inc.) to approximately 0.3 mg/ml.

Several methods may be used to obtain a large stock of Reelin for binding studies and screening assays. Bulk transient transfections can be carried out and several harvests of secreted Reelin can be prepared. Stable cell lines overexpressing Reelin can be generated using standard cell biology techniques in 293T or other mammalian cell systems (Hela, Jurkat, NIH3T3, or CHO). This will allow the continuous secretion of Reelin into the culture medium. In addition, viral vector systems such as baculoviruses can be used for Reelin production. Since we can readily detect Reelin by Coomassie Brilliant Blue staining using concentrated medium from transiently transfected cells, it will be possible to purify large quantities using a Bioreactor for cell culture.

Fusion proteins. Reelin fused to Alkaline Phosphatase or to a Myc epitope tag can bind to the VLDL receptor. This allows detection of binding activity either by assays for Alkaline Phosphatase enzymatic activity or immunological detection using a Myc epitope monoclonal antibody (9E10, Babco).

Expression of the VLDL Receptor. A cDNA clone of the human VLDL receptor was obtained (Oka et al., Genomics 20:298, 1994). To express the VLDL receptor, 293T or COS cells can be transfected with an expression construct containing the human VLDL receptor cDNA cloned into pcDNA3.1-Zeo (Invitrogen). Cells are transfected using the Fugene6 reagent in the same culture medium. Two days after transfection, cells can be analyzed for VLDL receptor expression levels using a polyclonal antiserum.

Reelin-VLDL receptor binding assay. 293T cells transfected with or without the VLDL receptor are washed in phosphate buffer saline (PBS) containing divalent cations and distributed into Eppendorf tubes (approximately $10^6$ cells/sample). For Reelin binding assays, cells are incubated with conditioned medium containing 20–100 ng of Reelin for 30 min to 2 h at 4° C. or room temperature. Cells are then washed again with PBS and solubilized in 40 ml of TxB buffer (150 mM NaCl, 50 mM Tris-Cl pH7.5, 1% Triton-X, 1 mM EDTA) supplemented with 0.1 mg/ml Aprotinin, with 0.1 mg/m Leupeptin, 20 mM Sodium Fluoride, and 1 mM Sodium Orthovanadate. Cell extracts are clarified by centrifugation at 13,000×g for 10 min at 4° C. and subjected to Western blot analysis to reveal the presence of Reelin retained by the VLDL receptor. No Reelin binding is observed in cells that do not express the VLDL receptor under the binding condition described here.

Western blot analysis. Ten $\mu$l of cell extract per lane are analyzed by SDS-PAGE on 4–12% minigels (Novex). Proteins are transferred to nitrocellulose membranes and blocked in 3% milk in Tris buffer saline (TBS) for 1 h at room temperature. Proteins bound to the membranes are incubated at 4° C. overnight in antibody diluted in 0.3% milk-TBS supplemented with 0.1% Tween (TBST). Ascites fluids containing the mouse monoclonal G10 antibody (de Bergeyck et al., J. Neurosci. Methods, 82:17–24, 1998) are used at a 1:1000 dilution to detect Reelin. For detection of the VLDL receptor, the rabbit polyclonal serum described above is used at a 1:1000 dilution. HRP-conjugated anti-mouse or anti-rabbit antibodies (Amersham) are used together with the primary antibodies at a 1:10,000 dilution. Membranes are washed extensively in TBST and developed by enhanced chemiluminescence (ECL) using a commercial kit (Super Signal, Pierce).

High throughput screening assay. Mammalian (HeLa, Jurkat, NIH3T3, CHO, COS, or 293T cells) or insect cells (Sf9) expressing the human VLDL receptor are produced in large scale using the expression constructs described above. Cells are seeded on microplate dishes, rinsed with phosphate buffered saline (PBS), and overlaid with medium containing Reelin-fusion proteins. Cells are then washed with PBS and solubilized in the well by the addition of a detergent-containing buffer such as TxB buffer supplemented with protease inhibitors. We have found that, under similar conditions, the binding of Reelin to the VLDL receptor is highly specific.

Microplate dishes are centrifuged to remove the insoluble material, and the soluble cellular proteins are analyzed to detect the presence of Reelin. The method of detection will vary depending upon the particular form of Reelin used in the binding assay. When Alkaline Phosphatase-Reelin fusion proteins are employed, detection can be accomplished using a colorimetric system to measure the enzymatic activity of Alkaline Phosphatase. Alternatively, immunodetection can be performed using antibodies against the Myc tag or against Reelin itself. Secondary antibodies conjugated to a fluorophor such as FITC or Texas Red, or antibodies conjugated to an enzyme such as Alkaline Phosphatase or Horse Radish Peroxidase can be employed. The staining is then analyzed using a fluorimeter or a spectrophotometer.

Cell-free binding assays. Purified Reelin protein and VLDLR protein or cell extracts containing VLDLR are obtained. One of these components (preferably VLDLR) is immobilized on beads, in microtiter wells, or on chips. The other (preferably Reelin) is detectably labeled (with an enzyme, reporter protein, radiolabel, fluorophore, etc.) used in soluble form. Reelin binding is detected as described above.

The cell-free approach has the advantage of rapid throughput screening.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values are approximate, and are provided for description.

All patents, patent applications, publications, and other materials cited herein are hereby incorporated herein reference in their entireties.

We claim:

1. A composition comprising an isolated Reelin polypeptide bound to an isolated low density lipoprotein receptor (LDLR), wherein Reelin is an extracellular glycoprotein of approximately 385 kDA containing a small region of similarity with F-spondin at the N terminus, a stretch of positively charged amino acids at the C terminus, and a series of eight internal repeats of 350–390 amino acids, each repeat containing two related sub-domains that flank a pattern of conserved cystine residues known as an EGF-like motif; wherein the composition is provided in a solution.

2. The composition of claim 1, wherein the Reelin polypeptide is selected from the group consisting of a 250K N-terminal fragment and a 150K N-terminal fragment.

3. The composition of claim 1, wherein the LDLR is a very low density lipoprotein receptor (VLDLR).

4. The composition of claim 3, further comprising a VLDLR peptide, wherein the VLDLR peptide interacts with Reelin or ApoE or both.

5. The composition of claim 1, wherein the Reelin polypeptide is detectably labeled.

6. The composition of claim 5, wherein the Reelin polypeptide is a fusion protein comprising a Reelin amino acid sequence and a non-Reelin amino acid sequence, which non-Reelin amino acid sequence comprises a peptide tag or a reporter protein.

7. The composition of claim 1, further comprising a test compound.

8. The composition of claim 1, wherein the Reelin polypeptide and the LDLR are cell-free.

9. The composition of claim 1, wherein the LDLR is located in the membrane of a recombinant host cell that does not endogenously express the LDLR.

10. The composition of claim 9, wherein the host cell is selected from the group consisting of a mammalian cell and an insect cell.

11. The composition of claim 10, wherein the host cell is a 293T cell.

12. The composition of claim 1, further comprising an ApoE polypeptide.

13. A screen for compounds that modulate Reelin binding to an LDLR, which screen comprises the composition of claim 1 in an assay system.

14. The screen of claim 13, wherein the assay system is a microplate array.

15. The screen of claim 14, further comprising an automated robotic microprocessor controlled system for adding and removing reagents to the microplate array.

16. The composition of claim 1, wherein the Reelin polypeptide is a protein having a sequence selected from the group consisting of SEQ ID NO:1 and SEQ ID NO:2.

17. The screen of claim 13, wherein the Reelin polypeptide is a protein having a sequence selected from the group consisting of SEQ ID NO:1 and SEQ ID NO:2.

* * * * *